(12) United States Patent
Otsuki et al.

(10) Patent No.: US 11,640,404 B2
(45) Date of Patent: May 2, 2023

(54) PROPERTY SEARCH APPARATUS, SYSTEM, METHOD, AND PROGRAM

(71) Applicant: TOYOTA JIDOSHA KABUSHIKI KAISHA, Toyota (JP)

(72) Inventors: Nobuhisa Otsuki, Toyota (JP); Issei Nakashima, Toyota (JP); Manabu Yamamoto, Toyota (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 375 days.

(21) Appl. No.: 16/908,981

(22) Filed: Jun. 23, 2020

(65) Prior Publication Data
US 2020/0409959 A1    Dec. 31, 2020

(30) Foreign Application Priority Data

Jun. 28, 2019   (JP) .............................. JP2019-121817

(51) Int. Cl.
| | |
|---|---|
| G06F 16/2457 | (2019.01) |
| G16H 20/30 | (2018.01) |
| G06F 16/23 | (2019.01) |
| G06F 16/248 | (2019.01) |
| G06Q 50/16 | (2012.01) |

(52) U.S. Cl.
CPC ........ *G06F 16/24575* (2019.01); *G06F 16/23* (2019.01); *G06F 16/248* (2019.01); *G06F 16/24578* (2019.01); *G16H 20/30* (2018.01); *G06Q 50/16* (2013.01)

(58) Field of Classification Search
CPC .............................. G06F 16/2457; G06F 16/23
See application file for complete search history.

(56) References Cited

U.S. PATENT DOCUMENTS

| | | |
|---|---|---|
| 2006/0190279 A1 | 8/2006 | Heflin |
| 2015/0342820 A1 | 12/2015 | Shimada et al. |
| 2017/0197111 A1* | 7/2017 | Mak ................... G09B 19/0038 |

FOREIGN PATENT DOCUMENTS

| | | |
|---|---|---|
| JP | 2001-297142 A | 10/2001 |
| JP | 2006-331363 A | 12/2006 |

(Continued)

OTHER PUBLICATIONS

"Image of Spatial Network Model for Pedestrians"; Ministry of Land, Infrastructure, Transport and Tourism; https://www.mlit.go.jp/common/001229548.pdf.

*Primary Examiner* — Truong V Vo
(74) *Attorney, Agent, or Firm* — Oliff PLC

(57) ABSTRACT

An appropriate property according to the physical ability of a trainee who has performed rehabilitation in order to restore or maintain his/her physical ability can be easily retrieved. A property search apparatus includes a reception unit configured to receive a property search request for a trainee who has performed training to restore or maintain his/her physical ability, an acquisition unit configured to acquire physical ability information of the trainee, a specification unit configured to specify, for each of a plurality of property candidates corresponding to the property search request, a location condition corresponding to the physical ability information by using a barrier-free map information, and an output unit configured to output a search result of the property candidates according to the specified location condition.

19 Claims, 15 Drawing Sheets

(56) References Cited

FOREIGN PATENT DOCUMENTS

| JP | 2015-223294 A | 12/2015 |
|----|---------------|---------|
| JP | 2019-045361 A | 3/2019  |
| JP | 2019-105632 A | 6/2019  |

* cited by examiner

|  | SIAS | | | | | |
|---|---|---|---|---|---|---|
|  | 0 | 1 | 2 | 3 | 4 | 5 |
| FIM 1 | A | A | B | C | C | C |
| 2 | A | A | B | C | C | C |
| 3 | B | B | B | C | D | D |
| 4 | C | C | C | C | D | D |
| 5 | C | C | C | C | D | E |
| 6 | C | D | D | D | D | E |
| 7 | C | D | D | E | E | E |

Fig. 3

PROPERTY SEARCH APPARATUS, SYSTEM, METHOD, AND PROGRAM

CROSS REFERENCE TO RELATED APPLICATIONS

This application is based upon and claims the benefit of priority from Japanese patent application No. 2019-121817, filed on Jun. 28, 2019, the disclosure of which is incorporated herein in its entirety by reference.

BACKGROUND

The present disclosure relates to a property search apparatus, a system, a method, and a program.

When a patient or the like performs rehabilitation (rehab or training) in order to restore or maintain his/her physical ability, he/she may use a rehabilitation support apparatus such as a walking training apparatus. As an example of a walking training apparatus, Japanese Unexamined Patent Application Publication No. 2015-223294 discloses a walking training apparatus including a walking assistance apparatus that is attached to a leg of a trainee and assists the trainee in walking.

SUMMARY

It should be noted that a patient (i.e., a trainee) under rehabilitation (hereinafter also referred to as a rehabilitation patient (or a rehabilitation trainee)) may have difficulty in his/her ordinary life when he/she returns to his/her house from a rehabilitation facility and leads the life in the house during or after the rehabilitation. In such a case, the rehabilitation patient may move from the house to a new one. However, it is difficult for a rehabilitation patient to find a real estate property suitable for his/her life because the degree of recovery of the rehabilitation patient widely differs from one patient to another, and the equipment in the property, the route to the property, and the like also widely differ from one property to another.

The present disclosure has been made in order to solve such a problem and an object thereof is to provide a property search apparatus, a system, a method, and a program for easily retrieving (i.e., finding) an appropriate property according to the physical ability of a trainee who has performed rehabilitation in order to restore or maintain his/her physical ability.

A first exemplary aspect is a property search apparatus including: a reception unit configured to receive a property search request for a trainee who has performed training to restore or maintain his/her physical ability; an acquisition unit configured to acquire physical ability information of the trainee; a specification unit configured to specify, for each of a plurality of property candidates corresponding to the property search request, a location condition corresponding to the physical ability information by using a barrier-free map information; and an output unit configured to output a search result of the property candidates according to the specified location condition.

Note that it can be considered that even for the same property, its location conditions such as a route from the property to a facility or the like near the property and a time required for getting to the facility (hereinafter also simply referred to as the required time) change as the restriction on the movement of the trainee changes depending on his/her physical ability. Therefore, in this embodiment, when the property search apparatus or the like searches for a property for a trainee who has performed training in order to restore or maintain his/her physical ability, it specifies a location condition(s) corresponding to physical ability information by using barrier-free map information and outputs a search result of property candidates according to the specified location condition. Therefore, it is possible to easily retrieve (i.e., find) an appropriate property according to the physical ability of a trainee who has performed rehabilitation in order to restore or maintain the physical ability.

Further, the property search apparatus may further include a first storage unit configured to store first definition information defining a barrier-free tolerance according to the physical ability. The specification unit may specify the barrier-free tolerance of the trainee from the acquired physical ability information based on the first definition information. The specification unit may specify, for each of the plurality of property candidates, the location condition by using the barrier-free map information so as to satisfy the specified barrier-free tolerance. By using the barrier-free tolerance corresponding to the physical ability as described above, it is possible to objectively specify the location condition according to the physical ability.

Further, the property search request may include a designation of a nearby facility in the vicinity of the property candidates. The specification unit may specify, from among walking routes between each of the plurality of property candidates and the nearby facility in the barrier-free map information, a walking route that satisfies the specified barrier-free tolerance as a walking route along which the trainee can walk. The specification unit may specify the location condition based on the specified walking route. The walking route between the candidate property and the nearby facility along which the trainee can walk changes depending on the physical ability, and the appropriate walking route for the trainee can be specified by using the barrier-free map information and the barrier-free tolerance. By doing so, it is possible to specify the location condition according to the physical ability.

Further, the barrier-free map information may include an attribute of the walking route. The specification unit may specify, from among the walking routes between each of the plurality of property candidates and the nearby facility, a walking route whose attribute satisfies the specified barrier-free tolerance as the walking route along which the trainee can walk. By using the attribute of the walking route, it is possible to specify an appropriate walking route according to the physical ability more accurately.

Alternatively, the property search request may include a designation of a nearby facility in the vicinity of the property candidates. The specification unit specifies a walking route between each of the plurality of property candidates and the nearby facility in the barrier-free map information based on the physical ability information, the walking route being a route along which the trainee can walk. The specification unit may specify the location condition based on the specified walking route. The walking route between the candidate property and the nearby facility along which the trainee can walk changes depending on the physical ability, and the appropriate walking route for the trainee can be specified by using the barrier-free map information and the physical ability information. By doing so, it is possible to specify the location condition according to the physical ability.

Further, the specification unit may calculate, for the specified walking route, a time required for the trainee to move along the specified walking route according to the physical ability information, and specify the calculated required time as the location condition. Even for the same walking route, it is possible to specify a more accurate location condition by using the required time in which the physical ability is taken into consideration.

Further, the property search apparatus may further include a search unit configured to transmit at least a part of the property search request to a property search server and receive the plurality of property candidates from the property search server. The specification unit may specify the location condition for each of the plurality of retrieved property candidates. In this way, there is no need to internally manage any property information database. That is, it is possible to search the latest property information by using an external property information database(s).

Further, the search unit may generate, from the at least the part of the property search request, a plurality of individual property search requests each of which corresponds to a respective one of two or more property search servers, and transmit, to each of the property search servers, its corresponding individual property search request, and the specification unit may make the plurality of property candidates by combining search results received from the property search servers. By summarizing search results of a plurality of external property search servers as described above, it is possible to obtain more complete property candidates and thereby provide a search result based on the location condition in which the physical ability is taken into consideration. Therefore, it is possible to provide an aggregation service by using a plurality of external property search servers.

Further, the property search apparatus may further include a charging unit configured to, when a contract is made with a trainee side including the trainee for a property candidate included in the output search result, charge the property search server that has retrieved the property candidate for which the contract has been made. In this way, it is possible to effectively obtain a monetary value for an added value that the search result is provided based on the location condition in which the physical ability is also taken into consideration as compared to search results of ordinary property search sites.

Further, the property search apparatus may further include a registration unit configured to, when a contract is made with a trainee side including the trainee for a property candidate included in the output search result, associate the property candidate for which the contract has been made with the acquired physical ability information and store them in a history storage device. The specification unit may specify the location condition by further taking information stored in the history storage device into consideration. By taking the history information into consideration, it is possible to specify a better location condition for a property candidate for which a contract has been made based on past search results. Therefore, it is possible to retrieve (i.e., find) an appropriate property according to the physical ability of a trainee more accurately.

Further, the property search apparatus may further include a first updating unit configured to collect data through a network, extract an attribute of a sidewalk from the collected data, and update the barrier-free map information, the data being data that is acquired when an IoT (Internet of Things) device is being moved. By automatically updating the barrier-free map information as described above, it is possible to efficiently extend the range of the barrier-free map information and efficiently improve the accuracy thereof.

Further, the property search apparatus may further include a second updating unit configured to collect contribute information about sidewalks through a network, extract a condition of the sidewalk from the collected contribution information, and update the barrier-free map information. By automatically updating the barrier-free map information as described above, it is possible to efficiently extend the range of the barrier-free map information and efficiently improve the accuracy thereof.

Further, the reception unit may further receive a request for an action as the trainee moves from a target property to a predetermined point, and the specification unit may specify the location condition so as to satisfy the request for the action. In this way, it is possible to retrieve a property candidate closer to the need of the trainee.

Further, the property search apparatus may further include a second storage unit configured to store second definition information defining barrier-free equipment information according to the physical ability. The specification unit may specify the barrier-free equipment information from the acquired physical ability information based on the second definition information, and specify property candidates each of which includes the barrier-free equipment information from among the plurality of property candidates. The output unit may output a search result of the property candidate from among the specified property candidates according to the specified location condition. In this way, it is possible to retrieve a property candidate equipped with equipment suitable for the physical ability.

Further, the physical ability information may include information about a harness used by the trainee. In this way, it is possible to specify an appropriate walking route while taking the harness into consideration, and obtain a required time therefor according to the harness. Therefore, it is possible to retrieve an appropriate property according to the physical ability of a trainee more accurately.

A second exemplary aspect is a property search system including: a first storage device configured to store a plurality of property information pieces; a second storage device configured to store barrier-free map information; and a property search apparatus connected to the first and second storage devices through a network, in which the property search apparatus includes: a reception unit configured to receive a property search request for a trainee who has performed training to restore or maintain his/her physical ability; an acquisition unit configured to acquire physical ability information of the trainee; a specification unit configured to specify, for each of a plurality of property candidates corresponding to the property search request, a location condition corresponding to the physical ability information by using the barrier-free map information; and an output unit configured to output a search result of the property candidates according to the specified location condition.

A third exemplary aspect is a method for searching for a property, including: receiving, by a computer, a property search request for a trainee who has performed training to restore or maintain his/her physical ability; acquiring, by the computer, physical ability information of the trainee; specifying, by the computer, for each of a plurality of property candidates corresponding to the property search request, a location condition corresponding to the physical ability information by using a barrier-free map information; and outputting, by the computer, a search result of the property candidates according to the specified location condition.

A fourth exemplary aspect is a property search program for causing a computer to perform: a process of receiving a property search request for a trainee who has performed training to restore or maintain his/her physical ability; a process of acquiring physical ability information of the trainee; a process of specifying for each of a plurality of property candidates corresponding to the property search request, a location condition corresponding to the physical ability information by using a barrier-free map information; and a process of outputting a search result of the property candidates according to the specified location condition.

Effects similar to those of the first aspect can also be expected in the second, third and fourth aspects.

According to the present disclosure, it is possible to provide a property search apparatus, a system, a method, and a program for easily retrieving an appropriate property according to the physical ability of a trainee who has performed rehabilitation in order to restore or maintain his/her physical ability.

The above and other objects, features and advantages of the present disclosure will become more fully understood from the detailed description given hereinbelow and the accompanying drawings which are given by way of illustration only, and thus are not to be considered as limiting the present disclosure.

BRIEF DESCRIPTION OF DRAWINGS

FIG. 3 shows a conversion table, which is an example of definition information according to the first embodiment;

DESCRIPTION OF EMBODIMENTS

Specific embodiments to which the present disclosure including the above-described aspects is applied are described hereinafter in detail with reference to the drawings. The same reference symbols are assigned to the same components throughout the drawings and duplicated explanations are omitted as appropriate for clarifying the explanation.

First Embodiment

Figure 1:
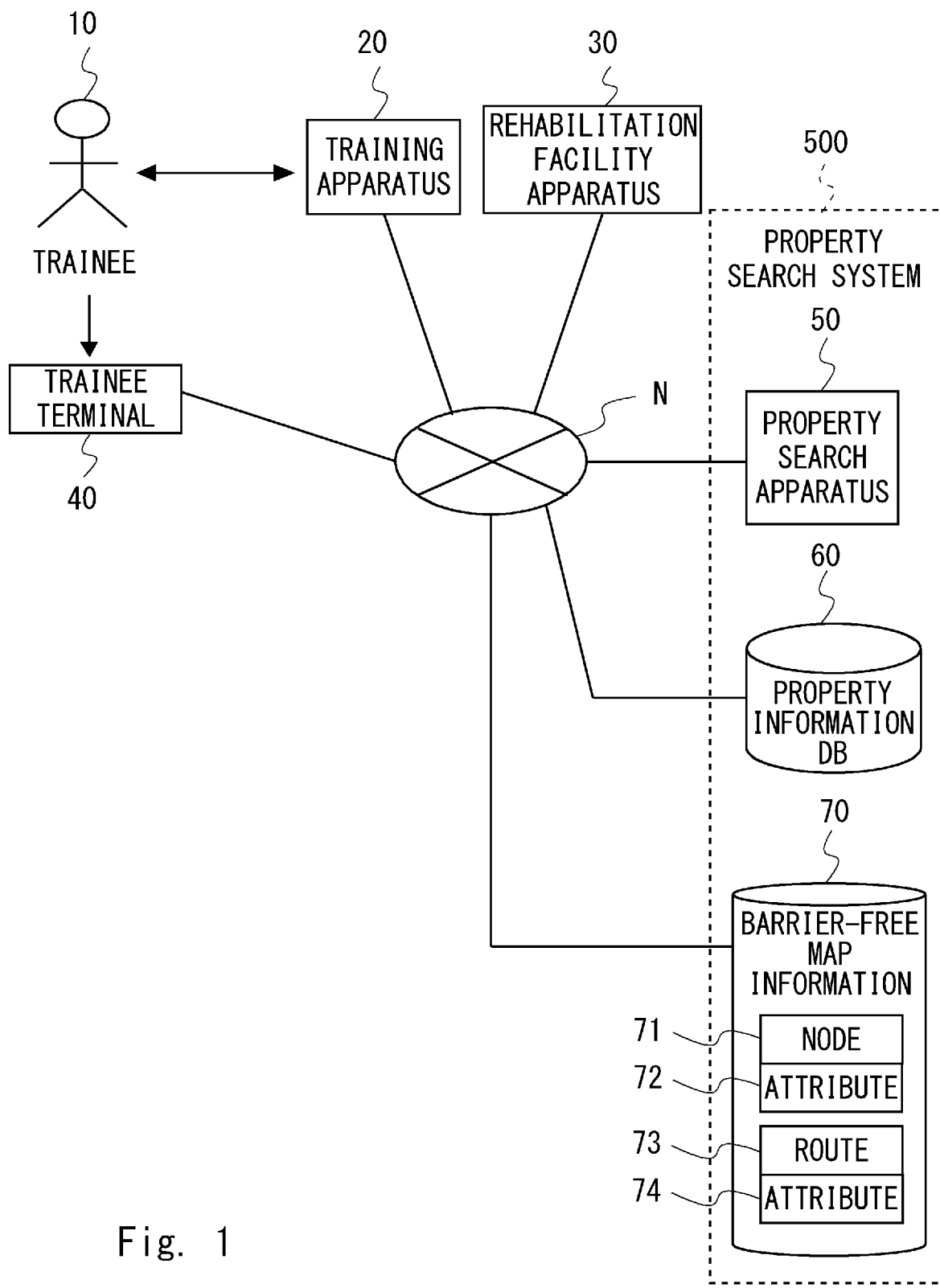
FIG. 1 is a block diagram showing an overall configuration of a property search system according to a first embodiment.

FIG. 1 is a block diagram showing an overall configuration including a property search system 500 according to a first embodiment. The property search system 500 includes a property search apparatus 50, a property information DB (DataBase) 60, and barrier-free map information 70. Further, these components are connected to a training apparatus 20 used by a trainee 10, a rehabilitation facility apparatus 30, and a trainee terminal 40 through a network N so that they can communicate with each other. Note that the network N is a communication line network such as the Internet, an intranet, a cellular phone network, and a LAN (Local Area Network).

The trainee 10 is a person who performs training in order to restore or maintain his/her own physical ability by using the training apparatus 20 or the like in a rehabilitation facility such as a medical institution. The trainee 10 is, for example, a rehabilitation patient who performs rehabilitation in order to restore his/her physical ability after surgery performed due to a serious illness or a serious injury. Alternatively, the trainee 10 is a person who performs rehabilitation to try to maintain his/her physical ability, such as an elderly person. Note that the term "rehabilitation" refers to a training process that is performed in order to restore or maintain a physical function or alleviate physical disability, irrespective of whether a health insurance is applied or not and whether a medical apparatus is used or not.

The training apparatus 20 is an apparatus by which the trainee 10 performs training in order to restore or maintain his/her physical ability in accordance with the assistance given by a training staff such as an instruction or help. As the training apparatus 20, for example, a rehabilitation support apparatus such as a walking training apparatus disclosed in Japanese Unexamined Patent Application Publication No. 2015-223294 can be used, though the training apparatus 20 is not limited to such rehabilitation support apparatuses.

In this case, the training apparatus 20 acquires detection data detected (measured) by internal or external sensors or the like during rehabilitation performed by the trainee 10. Note that the detection data is an example of the physical ability information and may be a set of measured values each of which corresponds to a respective one of a plurality of indexes (e.g., a plurality of sensors) for the measurement. Further, the detection data is data in which a measured value is associated with a measurement time and/or an index.

A typical example of the detection data is sensor data. The sensor data is sensor values detected by various sensors (not shown) of the training apparatus 20. For example, the sensor data includes an inclination angle of the trunk detected by the posture sensor, a load and an inclination angle detected by the handrail sensor, an angle detected by the angle sensor, etc. The sensors that output the sensor data are an acceleration sensor, an angular-velocity sensor, a position sensor, an optical sensor, a torque sensor, a weight sensor, etc. Further, encoders provided in motors of the winding mechanisms and the like included in the training apparatus 20 may be used as sensors. Further, a torque sensor (a load cell) of the motor may be used as a sensor, or a current detection unit that detects a driving current value for driving the motor may be used as a sensor.

Further, the sensor data may include, for example, line-of-sight data acquired by a line-of-sight detection sensor that detects a line of sight. Similar line-of-sight data can be obtained by detecting a line of sight of the trainee 10 by performing image processing based on an image taken by shooting at least an area including the eyes of the trainee 10, or obtained by determining the orientation (upward/downward etc.) of the face of the trainee 10 based on an image taken by shooting at least the face. Such data may also be included in the aforementioned detection data. Further, the detection data may be audio data (voice data) acquired by a voice acquisition unit, such as a microphone, that acquires a voice of the trainee 10 or the training staff, text data obtained by performing a voice analysis on the voice data, or data obtained by analyzing the text data. The voice of the training staff may include an encouraging talk to the trainee 10 about, for example, how to correct his/her walking. Further, the sensor data may be data obtained by detecting brain waves of the trainee 10 by using an electroencephalograph, or may be data obtained by detecting brain waves of the training staff by using an electroencephalograph.

Further, the line-of-sight detection sensor, a shooting unit that takes the above-described image, a microphone, and the like can be disposed in the training apparatus 20 itself. Alternatively, they can also be disposed in, for example, an eyeglass-type wearable terminal that is worn by the trainee 10. This terminal may include a wireless communication unit that wirelessly transmits and receives data by a wireless communication technique such as Bluetooth (Registered Trademark). Further, the training apparatus 20 may also include a wireless communication unit. In this way, the training apparatus 20 can acquire data acquired by the wearable terminal through wireless communication. Although the electroencephalograph is limited to those having high detection accuracy, it may be disposed in the training apparatus 20 itself and configured so that the electroencephalogram of the trainee 10 and that of the training staff can be separately detected. However, the electroencephalograph may be disposed at a position near the person whose brain waves are detected, such as being disposed in the above-described eyeglass-type wearable terminal (e.g., in a side frame of the eyeglasses).

Further, the detection unit that acquires detection data, such as sensors, is not limited to those described above. For example, the trainee 10 may wear clothes equipped with a wearable biosensor and/or a wearable touch sensor. Here, the clothes are not limited to those worn on the upper body. That is, they may be those worn on the lower body, a top-and-bottom set, or those attached to a part of the harness or the like. Further, a wireless communication unit like the one described above is provided in each of the clothes and the training apparatus 20. In this way, the training apparatus 20 can acquire data acquired by the wearable biological sensor or the wearable touch sensor through wireless communication. The wearable biosensor can acquire vital data such as the heart rate of the wearer. The wearable touch sensor can acquire data indicating information about a touch on the trainee 10, who is the wearer, made from the outside. That is, the wearable touch sensor can acquire data indicating information about a position where the training staff touched the trainee 10.

Further, the detection data is not limited to the values indicated by the detection signals detected by various sensors and the like. That is, they may include values calculated based on the detection signals from a plurality of sensors and statistical values obtained by statistically processing detection signals from one or a plurality of sensors or the like. As the statistical values, various statistical values such as an average value, a maximum value, a minimum value, and a standard deviation value may be used. Alternatively, they may be static statistical values or dynamic statistical values over a certain period such as one day, one training practice, or one walking cycle.

For example, the sensor data may include an open angle of the knee joint calculated from the angle between the upper-leg frame and the lower-leg frame detected by the angle sensor. Further, the sensor data of the angle sensor may include an angular velocity that is obtained by differentiate the angle. The sensor data of the acceleration sensor may be a velocity that is obtained by integrating the acceleration or a position that is obtained by integrating the acceleration twice.

For example, the detection data may include the below-described average value, the sum total value, the maximum value, the minimum value, and the representative value for each day or for each rehabilitation session on one day. Here, examples of the average value include an average speed (total walking distance/total walking time) [km/h], an average value of a stride length [cm], a walking rate [steps/min] indicating the number of steps per minute, a walking PCI [beats/m], and a falling-down prevention assistance [%]. The average speed may be, for example, a value calculated from a speed setting value of the treadmill or a value calculated from the drive signal in the treadmill drive unit. The stride length means a distance from where one heel touches the ground to where the same heel touches the ground again. The PCI means a Physiological Cost Index (a clinical indicator of a physiological cost index). The walking PCI indicates energy efficiency during the walking. The falling-down prevention assistance [%] means a rate corresponding to the number of times of falling-down prevention assistance [times] per step, i.e., the number of times the training staff has assisted the trainee 10 to prevent him/her from falling down per step. That is, the falling-down prevention assistance [%] means a rate at which falling-down prevention assistance actions are performed for each step.

Further, examples of the sum total value include a walking time [s], a walking distance [m], the number of steps [steps], the number of times of falling-down prevention assistance [times], and a falling-down prevention assistance part and the number of times for each part [times].

Further, examples of the maximum value or the minimum value include maximum values or minimum values of a continuous walking time [s], a continuous walking distance [m], the number of continuous steps [steps], and a minimum value of a walking PCI [beats/m] (in other words, a longest distance the trainee can walk per beat). Examples of the representative value include a speed of the treadmill that has been used most frequently (a representative speed [km/h]).

As described above, data supplied directly or indirectly from the detection unit such as various sensors can be included in the detection data. Further, time information such as date and time at which the detection is performed or timing information other than the time can be added to the above-described detection data.

Note that the above-described detection data is merely an example and other detection data may be used. Further, some of the above-described detection data may not be used.

Note that the physical ability information may include index data about rehabilitation performed by the trainee 10 by using the training apparatus 20, including at least one of a symptom, a physical ability, and a degree of recovery of the trainee 10. In other words, the physical ability information may include symptom information, a Br. Stage, a SIAS, an initial walking FIM, a latest walking FIM, and the like of the trainee 10. Note that the physical ability information may include various data indicating the physical ability of the trainee 10. Further, the index data of the trainee 10 may be determined or calculated by the training apparatus 20 itself, or may be evaluated by a training staff such as a doctor or a physical therapist, input through an input device (not shown), and stored in a storage device disposed in the training apparatus 20. Further, the physical ability information may include information about a harness used by the trainee.

Note that the symptom information may include information indicating an initial symptom, a time when the symptom appears, and a current symptom. Further, it can be considered that the trainee 10 needs to perform rehabilitation mainly because of at least one of the symptoms described above. However, symptoms that are unlikely to be directly related to the rehabilitation may also be included in the symptom information. Further, the symptom information may also include a type(s) of a disease(s) (a name(s) of a disease(s) or a disorder(s)) that the subject has suffered from, such as a stroke (a cerebrovascular disorder) and a spinal cord injury. Further, the symptom information may also include, depending on the type of the disease, its classification. For example, strokes can be classified into cerebral infarction, intracranial hemorrhage (cerebral hemorrhage/subarachnoid hemorrhage), etc.

The Br. Stage means a Brunnstrom Recovery Stage in which a recovery process of a hemiplegia is divided into six stages based on the observation. The trainee data may include, of the Br. Stage, lower-limb items that are main items related to the training apparatus 20. The SIAS means a Stroke Impairment Assessment Set, which is an index for comprehensively evaluating dysfunction caused by a stroke. The SIAS may include a hip flexion test (Hip-Flex), a knee extension test (Knee-Ext), and a foot-pat test (Foot-Pat). Further, the SIAS may also include a lower limb tactile sensation (Touch L/E), a lower limb position sensation (Position L/E), an abdominal muscle strength (Abdominal), and a verticality test (Verticality).

The FIM (Functional Independence Measure) is one of the evaluation methods for evaluating ADL (Activities of Daily Life). In the FIM, a patient is evaluated (i.e., classified) into seven stages, i.e., one point to seven points according to the level of assistance.

For example, a walking FIM is a general index indicating the degree of recovery. A patient who can walk 50 m or longer without an assistant and without a harness (an assisting device) receives the highest score of seven points. Further, a patient who can walk less than 15 m no matter how much assistance is provided by one assistant receives the lowest score of one point. Further, when a patient can move 50 m with the minimum assistance (an assistance level of 25% or lower), he/she receives four points, whereas when a patient can move 50 m with medium assistance (an assistance level of 25% or higher), he/she receives three points. Therefore, as the recovery progresses, the walking FIM of the trainee 10 gradually increases.

As can be understood from the above description, the latest walking FIM used by the training apparatus 20 is used as not only an index indicating the physical ability of the trainee 10 but also an index indicating the degree of recovery of the trainee 10 from the start of the rehabilitation. In other words, the walking FIM is an important index in order to recognize the progress of the rehabilitation of the trainee 10. Further, the amount of change from the initial walking FIM to the latest walking FIM or its changing speed is also used as an index indicating the degree of recovery. The change speed may also be referred to as FIM efficiency. For example, the changing speed may be a value that is obtained by dividing the gain (the amount of change) up to the current FIM by, for example, the number of days of the rehabilitation, the number of elapsed days indicating a period of the rehabilitation, or the number of days the patient has been hospitalized in the case where the trainee 10 is a hospitalized patient.

Further, the walking FIM can be regarded as a score that is obtained under the condition at the time of the evaluation, such as when the patient wears the harness. In this case, information indicating the condition applied at the time of the evaluation may be added in the information indicating the walking FIM. The condition may include a condition at the time when the information is acquired, such as a wedge thickness, a used harness (e.g., with other walking assistance apparatuses, without any harness, etc.), a setting such as an angular setting of a part of the knee or the ankle in the harness, and/or whether the walking is performed on a level ground or on a slope. Further, in general, the walking FIM means a walking FIM in walking on a level ground. Further, level-ground walking information indicating such walking FIM may include information such as the longest distance that the patient has walked (the maximum continuous walking distance [m]) in the evaluation of the level-ground walking.

Note that in general, data that can be included in both concepts of the physical ability and the degree of recovery, such as the latest walking FIM, may be included in one of them. However, such data can also be included in both of them.

Further, the training apparatus 20 may associate trainee attribute information such as an attribute and physical information of the trainee 10 with the above-described physical ability information and store them in an internal storage device. Note that the trainee attribute information may include an age, a gender, a physique (a height, a weight, etc.), and the like of the trainee 10. Further, the trainee attribute information may also include a name or an ID of the trainee 10. Further, the trainee attribute information may also include preference information indicating a preference of the trainee 10 and personality information indicating his/her personality. Further, the trainee attribute information may include, as the FIM, a movement item other than those related to the walking ability, and may include a cognitive item. Note that part or all of the physical ability information and/or the trainee attribute information may be referred to as physical information, basic information, or trainee feature information. Note that the training apparatus 20 may acquire the index data, the trainee attribute information, and the like by using an electronic medical record system (not shown) in a medical institution or the like, or by having a training staff enter such data.

Further, the training apparatus 20 may associate the trainee attribute information or the like with the physical ability information such as the detection data or the index data and store them in a storage device disposed inside the training apparatus 20. Alternatively, the training apparatus 20 may transmit the physical ability information and the like to the rehabilitation facility apparatus 30 through the network N and store them in a storage device disposed inside the rehabilitation facility apparatus 30. Alternatively, the training apparatus 20 may transmit the physical ability information and the like to the property search apparatus 50 through the network N in response to an operation performed by the training staff or the like, upon detection of detection data, at predetermined intervals, or in response to an acquisition request from the property search apparatus 50.

The rehabilitation facility apparatus 30 is an information processing apparatus installed in a facility where the trainee 10 performs rehabilitation by using the training apparatus 20, such as a medical institution, or installed in or at least operated by a facility where the rehabilitation is managed. The rehabilitation facility apparatus 30 is a database system that manages at least the physical ability information and the like.

For example, the rehabilitation facility apparatus 30 receives the physical ability information and the trainee attribute information which have been acquired from the training apparatus 20 through the network N. Then, the rehabilitation facility apparatus 30 associates the received physical ability information with the trainee attribute information and stores them in an internal storage device. Further, the rehabilitation facility apparatus 30 may acquire detection data from the training apparatus 20 through the network N, and acquire the index data, the trainee attribute information, and the like by using an electronic medical record system (not shown) in a medical institution or the like, or by having a training staff enter such data. Alternatively, when the trainee 10 performs training by using an apparatus or the like other than the training apparatus 20, the rehabilitation facility apparatus 30 may acquire data corresponding to the above-described detection data by having a training staff enter the data.

Further, the rehabilitation facility apparatus 30 may also transmit the physical ability information and the like to the property search apparatus 50 through the network N in response to an operation performed by the training staff or the like, upon acquisition of the physical ability information or the like, at predetermined intervals, or in response to an acquisition request from the property search apparatus 50. Note that since the configuration of the rehabilitation facility apparatus 30 can be implemented by a publicly-known information system or the like, its detailed description is omitted.

The trainee terminal 40 is an information processing apparatus operated by a user on the trainee side. Examples of the user include a relative, a guardian, and the like of the trainee 10 as well as the trainee 10 himself/herself. The trainee terminal 40 has a function of performing communication through the network N, and is, for example, a personal computer or a portable information terminal such as a tablet terminal, a smartphone, and the like. The trainee terminal 40 receives a real estate property search request (i.e., a request for searching for a real estate property) through an input device according to an operation performed by a user on the trainee side, and transmits the received property search request to the property search apparatus 50 through the network N. Further, the trainee terminal 40 receives a search result of property candidates from the property search apparatus 50 through the network N, and outputs (e.g., displays) the received search result to an output device such as a screen.

The property search apparatus 50 is composed of at least one information processing apparatus by which a trainee who has performed rehabilitation searches for a real estate property which is suitable for his/her after-training physical ability and to which the trainee will move. The property search apparatus 50 is, for example, a server apparatus. Further, it is assumed that in the property search apparatus 50, a web server, an application server, and a database server are executed on an OS (Operating System), and a web application for carrying out a property search process according to this embodiment is performed on the application server. However, the software configuration of the property search apparatus 50 is not limited to the above-described example. Further, details of the configuration of the property search apparatus 50 will be described later.

The property information DB 60 is an example of the first storage device and is a database system that manages information about real estate properties (for rent and for sale). The property information DB 60 receives a property search request through the network N and sends back property candidates corresponding to (i.e., suitable for) the property search request as a search result to the entity or the like that has transmitted the property search request through the network N. Note that the property information includes at least one of identification information of the property, a rent, a floor plan (a size (an area)), an age of the building, a type of the building, a structure, an attribute of the property, a nearest station, a required time for traveling from the nearest station to the property (hereinafter also simply referred to as the required time), etc. Further, the property information may include a designation of a barrier-free compatible as an attribute of the property. Further, the property information may include detailed information of the property such as housing equipment, an arrangement of furniture, an outdoor state (a passage to a garden), a design plan of the house, the number of steps to the front door, the presence/absence of a garden, the size of the garden, the shape of the garden, a specification of a water section (a toilet, a bath, and a kitchen), and the size of the water section.

The barrier-free map information 70 is information about a map of sidewalks, and in particular is a database system containing barrier-free information. The barrier-free map information 70 is an example of the second storage device, and is, for example, an information system that stores walking space network data or data equivalent thereto promoted by the Ministry of Land, Infrastructure, Transport and Tourism, and manages the walking space network data or the like. The barrier-free map information 70 includes nodes 71 for specifying points on the map and routes 73 of sidewalks along which people walk between the nodes. Further, for each node 71, an attribute 72 of the node is associated with its identification information (ID). The attribute 72 of the node includes, for example, a latitude, a longitude, and a floor level (a ground level or an underground level, a floor number). Further, for each route 73, an attribute 74 of the route is associated with its identification information (ID). The route 73 is expressed by a pair of a start-point node ID and an end-point node ID. Note that the attribute 74 of the route may also be referred to as an attribute of a walking route or an attribute of s sidewalk. Examples of the attribute 74 of the route include, but are not limited to, a difference in level on a sidewalk, a width of the sidewalk, an inclination of the sidewalk, presence/absence of a handrail, a length of the handrail, a height of the handrail, presence/absence of a roof, a height of the roof, and so on. Further, examples of the attribute 74 of the route also include a length of the route, a structure of the route, a type of the route, a direction, a width, a longitudinal slope, a difference in level, information about a pedestrian signal, a block or the like for guiding a visually handicapped person, a type of an elevator, presence/absence of a roof, and so on. Further, information in http://www.mlit.go.jp/common/001229548.pdf may be used.

Figure 2:
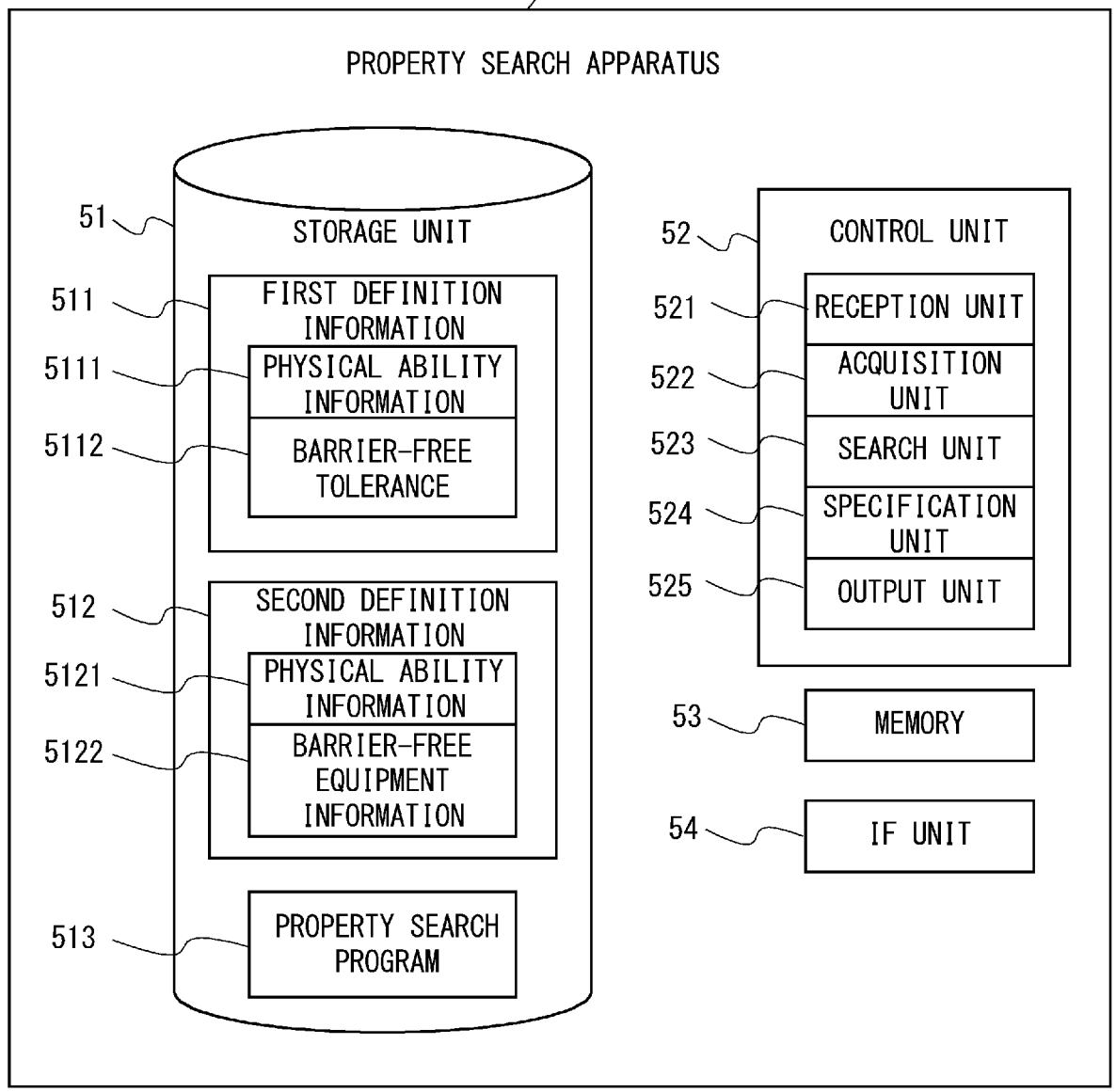
FIG. 2 is a block diagram showing a configuration of a property search apparatus according to the first embodiment.

FIG. 2 is a block diagram showing a configuration of a property search apparatus 50 according to the first embodiment. Note that FIG. 2 shows a functional block showing an internal configuration of the property search apparatus 50 when it is implemented by using one computer apparatus.

The property search apparatus 50 includes a storage unit 51, a control unit 52, a memory 53, and an IF (interface) unit 54. The storage unit 51 is an example of the first and second storage units, and is, for example, a nonvolatile storage device such as a hard disk drive and a flash memory. The storage unit 51 stores at least first definition information 511, second definition information 512, and a property search program 513.

The first definition information 511 is information defining a barrier-free tolerance according to the physical ability. In particular, the first definition information 511 according to this embodiment is association information in which the physical ability information 5111 is associated with the barrier-free tolerance 5112. For example, the first definition information 511 may be a conversion table or a conversion map defining a conversion rule from the physical ability information 5111 to the barrier-free tolerance 5112. In this case, the first definition information 511 may include a plurality of conversion tables each of which corresponds to a respective one of a plurality of types of the physical ability information 5111. Alternatively, the first definition information 511 may be a converter that converts physical ability information 5111 into barrier-free tolerance 5112, a function for obtaining barrier-free tolerance 5112 by using physical ability information 5111 as an input, a conversion algorithm, or a trained conversion model.

Note that the physical ability information 5111 includes a measured value(s) that is measured when the trainee 10 performs training by using the training apparatus 20 (i.e., includes a result of the training). The result of the training is, for example, the above-described detection data and/or sensor data detected by the training apparatus 20, and may be a set of measured values for a plurality of indexes. Further, the training includes walking training and trunk balancing (balance training), and in this case, the physical ability information 5111 includes results of these training items.

Further, the physical ability information 5111 includes an index value of the physical ability of the trainee 10 during or after the training, or a physical evaluation value determined based on the result of the training. The physical evaluation value includes, for example, the aforementioned Br. Stage, the SIAS, the initial walking FIM, the latest walking FIM, and the like. Therefore, the first definition information 511 may be one in which the physical evaluation value is associated with the housing equipment information.

The barrier-free tolerance 5112 is information indicating a degree of a barrier-free state to which the trainee 10 is tolerant with his/her physical ability indicated by his/her physical ability information. Specifically, the barrier-free tolerance 5112 is a threshold for a barrier-free level which indicates a compliance degree of a barrier-free state indicated by the attribute of the sidewalk.

Further, the first definition information 511 may be one in which a plurality of indexes of the physical ability information 5121 are associated with the barrier-free tolerance 5112. FIG. 3 shows a conversion table, which is an example of the first definition information 511 according to the first embodiment. An example in which two indexes FIM and SIAS are used as a plurality of indexes is shown hereinafter. For example, the walking FIM is represented by values 1 to 7 and the SIAS in a lower-leg distal test is represented by values 0 to 5. Further, a combination of a FIM value and a SIAS value is associated with one of barrier-free tolerances A to E. For example, regarding the barrier-free tolerance A, the degree of independence of the FIM is low and the SIAS is also low, so that it indicates the highest one as the compliance level of the barrier-free state. In this case, for example, since the trainee 10 uses a wheelchair and is likely to be accompanied by an assistant, the required attribute (of the equipment) of the walking route may include an elevator, a slope, a roof, and the like, and may include those in a high rank. In contrast, regarding the barrier-free tolerance B, the degree of independence indicated by the FIM and SIAS is higher than that of the barrier-free tolerance A. Therefore, the elevator is excluded from the required attribute of the walking route (since it is not indispensable), and a slope and a handrail are included in the attribute. Further, the rank of the slope may possibly decrease. That is, the rank of the required attribute of the walking route changes according to the change in the degree of independence indicated by the combination of the FIM and the SIAS. However, the barrier-free tolerance in the highest rank does not necessarily include the highest-level equipment in each category of the attribute (of the equipment) of the walking route. In the above-described example, there may be a case where although the barrier-free tolerance B includes a handrail, the barrier-free tolerance A does not necessarily require a handrail because the trainee 10 cannot walk by himself/herself.

The second definition information 512 is information defining barrier-free equipment information according to the physical ability. In particular, the second definition information 512 according to this embodiment is association information in which physical ability information 5121 is associated with the barrier-free equipment information 5122. For example, the second definition information 512 may be a conversion table or a conversion map defining a conversion rule from the physical ability information 5121 to the barrier-free equipment information 5122. In this case, the second definition information 512 may include a plurality of conversion tables each of which corresponds to a respective one of a plurality of types of the physical ability information 5121. Alternatively, the second definition information 512 may be a converter that converts physical ability information 5121 into barrier-free equipment information 5122, a function for obtaining barrier-free equipment information 5122 by using physical ability information 5121 as an input, a conversion algorithm, or a trained conversion model.

The barrier-free equipment information 5122 includes at least one of identification information of housing equipment, a product type, a rank in the type, a specification of the housing equipment, an installation condition, setting information, and a detail of a construction work of the housing equipment in the real estate property (such as an apartment, a condominium, and a detached house). Note that examples of the housing equipment include so-called housing equipment for a barrier-free compliance such as a handrail, a slope, flooring (for eliminating a difference in level on the floor) and a handrail in a bathroom, an outdoor passage, furniture, an electric appliance, and so on. The identification information of the housing equipment, the product type, the rank in the type, and the specification of the housing equipment may be acquired from, for example, a database for equipment managed by a renovation company or a real-estate agent. Note that the rank of the housing equipment is information indicating a difference in the grade such as a price, a specification, or the like in housing equipment of the same type. That is, in the second definition information 512, a different physical evaluation value may be associated with each of a plurality of ranks in the housing equipment of the same type. In this way, it is possible to not only present the housing equipment such as a "slope", but also present the housing equipment in an appropriate rank according to the physical evaluation value.

The installation condition is, for example, information such as a length, a height, an inclination, an angle, and an installation place (e.g., outside the front door or inside the front door) of the slope. Alternatively, in the case where a wheelchair can move more easily by changing an arrangement of existing furniture, the installation condition may include information about the arrangement of existing furniture. The setting information is information indicating a detail of a setting of an electric appliance. For example, when the electric appliance is an HSR (Human Support Robot), the setting information is a detail of a setting for providing support suitable for the physical ability information 5121 of the trainee 10. Further, when the electric appliance is a smart speaker equipped with a camera, the setting information is a detail of a setting of its software. Further, when the electric appliance is a camera, the setting information is, for example, a detail of a setting such as a setting for turning on a tipping-over detection function. Examples of the detail of the construction work of the housing equipment include a construction work for extending a bathroom and a detail of that construction work.

Further, the second definition information 512 may be one in which a plurality of indexes of the physical ability information 5121 are associated with the barrier-free equipment information 5122. Note that the conversion table, which is an example of the second definition information 512 according to the present first embodiment, may be the same as the above-described table shown in FIG. 3, and therefore the drawing thereof is omitted. An example in which two indexes FIM and SIAS are used as a plurality of indexes is shown hereinafter. For example, the walking FIM is represented by values 1 to 7 and the SIAS in a lower-leg distal test is represented by values 0 to 5. Further, a combination of a FIM value and a SIAS value is associated with one of sets A to E of the housing equipment information. For example, regarding the set A of the housing equipment information, the degree of independence of the FIM is low and the SIAS is also low, so that it indicates the highest set of the housing equipment information. In this case, for example, since the trainee 10 uses a wheelchair and is likely to be accompanied by an assistant, the housing equipment information may include an elevator, a slope, and the like, and may include those having a high rank among them. In contrast, regarding the set B of the housing equipment information, the degree of independence indicated by the FIM and the SIAS is higher than that of the set A. Therefore, the elevator is excluded from the housing equipment information, and a slope and a handrail are included in the housing equipment information. Further, the rank of the slope may possibly decrease. That is, the rank of a set of the housing equipment information changes according to the change in the degree of independence indicated by the combination of the FIM and the SIAS. However, the set of the housing equipment information having the highest rank does not necessarily include the whole housing equipment. In the above-described example, there may be a case where although the set B of the housing equipment information includes a handrail, the set A of the housing equipment information does not necessarily require a handrail because the trainee 10 cannot walk by himself/herself.

Further, the FIM includes intermediate items such as self-care, excretion, a transfer (from one vehicle to another), and a transfer (from one place to another) as movement items, and each of the intermediate items includes a plurality of sub-items. Further, the FIM also includes intermediate items such as communication and social recognition as cognitive items, and each of the intermediate items includes a plurality of sub-items. It should be noted that some of movements specified by a plurality of sub-items belonging to one intermediate item may be the same as (or similar to) those specified by sub-items belonging to other intermediates. For example, a movement of a sub-item "toilet movement" belonging to an intermediate item "self-care" is highly relevant to that of a sub-item "toilet" belonging to an intermediate item "transfer (from one vehicle to another)". Therefore, the second definition information 512 may define association between a combination of the FIM of the sub-item "toilet movement" and the FIM of the sub-item "toilet" and barrier-free equipment information 5122 such as a handrail in a toilet. That is, the second definition information 512 may include association between some of the combinations of the plurality of indexes and the barrier-free equipment information 5122. In this case, the second definition information 512 may include a conversion table for each of the some of the combinations of the plurality of indexes. In this way, it is possible to specify a property equipped with barrier-free equipment more suitable for the physical ability information including various indexes by using the second definition information 512.

Note that in the second definition information 512, a degree of rise in the physical evaluation value may be associated with the barrier-free equipment information 5122. For example, the second definition information 512 may include a definition of housing equipment information by which a physical assessment value, which is determined based on the result of the training of the trainee 10, may be raised.

The description is continued by referring to FIG. 2 again. The property search program 513 is a computer program in which processes that are performed in a method for searching for a property according to the first embodiment are implemented.

The memory 53 is a volatile storage device such as a RAM (Random Access Memory) and includes a storage area for temporarily storing information during the operation of the control unit 52.

The IF unit 54 is an interface for externally inputting/outputting data to/from the property search apparatus 50. The IF unit 54 is a communication circuit for performing at least communication through the network N.

The control unit 52 is a processor for controlling each component/structure of the property search apparatus 50. The control unit 52 loads a property search program 513 from the storage unit 51 into the memory 53 and executes the loaded property search program 513. In this way, the control unit 52 implements functions of a reception unit 521, an acquisition unit 522, a search unit 523, a specification unit 524, and an output unit 525 (all of which will be described below).

The reception unit 521 receives a property search request (i.e., a request for searching for a property) for the trainee 10. For example, the reception unit 521 receives a property search request including a search condition(s) for a property where the trainee 10 will live from the trainee terminal 40 through the network N. Examples of the search condition include at least one of a rent, a floor plan (a size (an area)), an age of the building, a type of the building, a structure, an attribute of the property, a nearest station, a required time for traveling from the nearest station to the property (hereinafter also simply referred to as the required time), etc. Further, the search condition according to this embodiment may include a designation of a barrier-free compatible as an attribute of the property. Further, the search condition may include a designation of a nearby facility in the vicinity of the property candidate. Examples of the nearby facility include, but are not limited to, facilities and the like that the trainee 10 needs to use on a daily basis such as a station of a public transportation system (such as a nearest railway station and a bus stop), a store, a medical institution, and a rehabilitation facility. Further, the search condition may include a request for an action as the trainee moves from a target property to a predetermined point. The request for an action means that, for example, the trainee 10 should be able to move to the above-described nearby facility by himself/herself or with an assistant.

Further, the reception unit 521 may further acquire input information of at least one of physical information of the trainee 10 and assistant information related to the trainee 10. Examples of the physical information include the above-described trainee attribute information. Further, the assistance information is information indicating a person(s) who may assist the trainee 10 when he/she lives in the property (e.g., a housemate such as a family member and a relative, a care worker, and a care manager), the number of these persons, a time period during which they can assist, a degree of assistance, and the like.

The acquisition unit 522 acquires physical ability information of the trainee 10. For example, the acquisition unit 522 acquires physical ability information of the trainee 10 from the training apparatus 20 or the rehabilitation facility apparatus 30 through the network N. Alternatively, the acquisition unit 522 may receive an input of physical ability information by an operation performed by a user through an input device directly connected to the property search apparatus 50 or through a computer connected thereto through a LAN or the like.

Alternatively, the acquisition unit 522 may acquire, from each of a plurality of training apparatuses used for the training, physical ability information stored in that training apparatus. For example, when one trainee 10 performs training using a plurality of training apparatuses 20, training results, physical evaluation values, and the like may be stored in each of the plurality of training apparatuses in a distributed manner. Alternatively, training results, physical evaluation values, and the like of training performed by a plurality of trainees 10 by using the same training apparatus 20 or different training apparatuses 20 may be stored in each of the plurality of training apparatuses in a distributed manner. In such a case, the acquisition unit 522 may collect the training results, the physical evaluation values, and the like from the plurality of training apparatuses 20 and store them in the storage unit 51. In this case, the storage unit 51 can be used as a database of the physical ability information 5111 and 5121, and can be used for various analyses and/or for the maintenance or the like of the first and second definition information 511 and 512.

Further, the acquisition unit 522 may acquire a current value of the physical evaluation determined based on the result of the training as the physical ability information, and further acquire a target value of the physical evaluation at the time when the trainee 10 is in the house. Alternatively, the acquisition unit 522 may acquire a plurality of measured values measured by the training apparatus 20 used for the training as the physical ability information.

The search unit 523 searches the property information DB 60 according to the property search request received by the reception unit 521 and acquires property candidates as a search result. Note that the search unit 523 may use at least a part of the search condition of the property search request as a search request.

For each of a plurality of property candidates corresponding to the property search request, the specification unit 524 specifies a location condition according to the physical ability information by using the barrier-free map information 70. Note that the location condition is information including a distance between the property candidate and a nearby facility, a time required to travel therebetween, and the like. Specifically, based on the first definition information 511, the specification unit 524 specifies a barrier-free tolerance 5112 of the trainee 10 from the physical ability information acquired by the acquisition unit 522. Then, the specification unit 524 specifies, for each of the plurality of property candidates, a location condition by using the barrier-free map information 70 so as to satisfy the specified barrier-free tolerance 5112.

For example, when index values of a plurality of indexes are included in the physical ability information, the specification unit 524 specifies a barrier-free tolerance 5112 from the first definition information 511 based on a combination of index values. For example, in the case where the above-described conversion table shown in FIG. 3 is used, the specification unit 524 specifies a barrier-free tolerance 5112 that is associated with, as a combination of a plurality of indexes, a combination of a FIM and a SIAS.

More specifically, the specification unit 524 specifies, from among walking routes between each of a plurality of property candidates and a nearby facility in the barrier-free map information 70, a walking route that satisfies the specified barrier-free tolerance 5112 as a walking route along which the trainee 10 can walk. Further, the specification unit 524 specifies a location condition based on the specified walking route. In particular, the specification unit 524 may specifies, from among the walking routes between each of the plurality of respective property candidates and the nearby facility, a walking route whose attribute satisfies the specified barrier-free tolerance 5112 as the walking route along which the trainee 10 can walk.

Further, from another viewpoint, it can be considered that the specification unit 524 specifies a walking route along which the trainee 10 can walk between each of a plurality of property candidates and a nearby facility in the barrier-free map information 70 based on the physical ability information. Further, the specification unit 524 specifies a location condition based on the specified walking route.

Then, the specification unit 524 calculates, for the specified walking route, a time required for the trainee 10 to travel along the specified walking route according to the physical ability information, and specifies the calculated required time as a location condition.

Further, when the reception unit 521 receives a request for an action, the specification unit 524 specifies a location condition so as to satisfy the request for the action. That is, the specification unit 524 specifies a walking route between a nearby facility indicated by the request for the action and the property candidate according to the physical ability information, and specifies a location condition based on the specified walking route.

The specification unit 524 may specify barrier-free equipment information 5122 from the physical ability information acquired by the acquisition unit 522 based on the second definition information 512, and specify a property candidate including the barrier-free equipment information 5122 from among the plurality of property candidates.

The specification unit 524 specifies, from the input information (at least one of a request for a movement, physical information, and assistant information) received by the reception unit 521 in addition to the property search request, barrier-free tolerance 5112 by using the first definition information 511 and specifies barrier-free equipment information 5122 by using the second definition information 512.

Further, when the first and second definition information 511 and 512 are defined by the physical evaluation value such as the FIM, the acquisition unit 522 may acquire a set of a plurality of measured values as a training result. In this case, the specification unit 524 determines a current physical evaluation value of the trainee 10 from the plurality of measured values, specifies the barrier-free tolerance 5112 associated with the current physical evaluation value by referring to the first definition information 511, and specifies the barrier-free equipment information 5122 associated with the current physical evaluation value by referring to the second definition information 512. In this way, even when the physical ability information (such as detection data) is not directly defined in the first and second definition information 511 and 512, the specification unit 524 can specify an appropriate barrier-free tolerance 5112 and barrier-free equipment information 5122. Note that a conversion table that is separately defined in advance may be used in the above-described method for determining a current physical evaluation value of the trainee 10 from a plurality of measured values.

The output unit 525 outputs a search result of property candidates according to the location condition specified by the specification unit 524. For example, the output unit 525 sorts (i.e., rearranges) the plurality of property candidates according to the location condition and outputs a result of the sorting as a search result.

Further, the output unit 525 displays the search result in a display apparatus such as a screen connected to the property search apparatus 50. Further, the output unit 525 transmits the search result to the trainee terminal 40 through the network N. Alternatively, the output unit 525 may transmit the search result to an information terminal (not shown) operated by an occupational therapist (OT) and/or the rehabilitation facility apparatus 30 through the network N. For example, an occupational therapist in charge of the rehabilitation of the trainee 10 can recognize a work necessary for a life after the training and after the start of the after-house-moving life by checking the detail of the property, to which the trainee 10 may move, and its location condition included in the search result, and can give a support to appropriately make a rehabilitation plan for the trainee 10.

Note that each of the above-described reception unit 521, the acquisition unit 522, the search unit 523, the specification unit 524, and the output unit 525 may be implemented by dedicated hardware. Further, some or all of the components of each unit may be implemented by a general-purpose or special-purpose circuit (circuitry), a processor or the like, or a combination thereof. They may be formed by a single chip, or may be formed by a plurality of chips connected to each other through a bus. Some or all of the components of each unit may be implemented by a combination of the above-described circuit or the like and a program. Further, as the processor (the control 52), a CPU (Central Processing Unit), a GPU (Graphics Processing Unit), an FPGA (field-programmable gate array), or the like may be used.

Further, when some or all of the components of the property search apparatus 50 are implemented by a plurality of information processing apparatuses, circuits, or the like, the plurality of information processing apparatuses, the circuits, or the like may be disposed in one place or arranged in a distributed manner. For example, the information processing apparatuses, the circuits, and the like may be implemented as a client-server system, a cloud computing system or the like, or a configuration in which the apparatuses or the like are connected to each other through a communication network. Alternatively, the functions of the property search apparatus 50 may be provided in the form of SaaS (Software as a Service).

Further, the storage unit 51 may be provided as a storage device located outside the property search apparatus 50, and may input/output data to/from the property search apparatus 50 by using a storage system, a database system, or the like.

Figure 4:
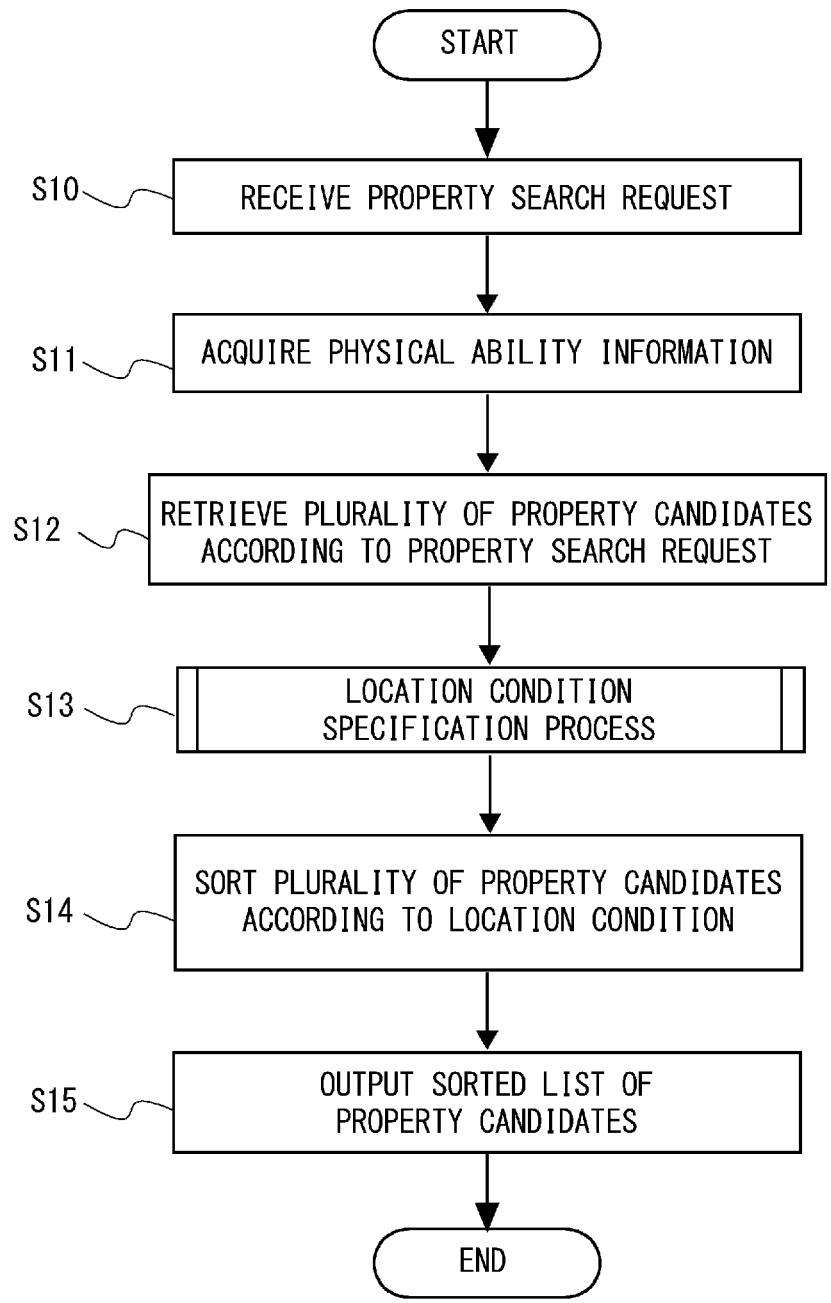
FIG. 4 is a flowchart showing a flow of a property search process according to the first embodiment.

FIG. 4 is a flowchart showing a flow of a property search process according to the first embodiment. For example, a user on the trainee side operates the trainee terminal 40 and thereby enters a request to search for a property (hereinafter also referred to as the property search request) including a search condition(s) (i.e., a condition(s) for searching) for a property to which the trainee may move in order to start a life of the trainee 10 after the training. Further, the trainee terminal 40 transmits the entered property search request to the property search apparatus 50 through the network N. Alternatively, a user of the property search apparatus 50 operates an information processing apparatus connected to the property search apparatus 50 in response to a request from the trainee side or the like and thereby enters the above-described property search request, and the information processing apparatus outputs the entered property search request to the property search apparatus 50.

The reception unit 521 of the property search apparatus 50 receives the property search request from the information terminal or the information processing apparatus such as the trainee terminal 40 or the rehabilitation facility apparatus 30 (S10). Note that the property search request includes at least identification information of the trainee 10 and includes a designation of a nearby facility in the vicinity of the property candidate as the above-described search condition. Further, the property search request may also include at least one of a request for an action from a property of interest by the trainee, physical information, and assistant information.

Next, the acquisition unit 522 of the property search apparatus 50 externally acquires physical ability information corresponding to the identification information of the trainee 10 included in the property search request (S11). For example, the acquisition unit 522 transmits a request to acquire physical ability information corresponding to the identification information of the trainee 10 (hereinafter also referred to as the acquisition request) to the training apparatus 20 or the rehabilitation facility apparatus 30 through the network N. Then, the acquisition unit 522 receives physical ability information that is sent back in response to the acquisition request from the training apparatus 20 or the rehabilitation facility apparatus 30 through the network N.

Then, the search unit 523 of the property search apparatus 50 searches for a plurality of property candidates from the property information DB 60 according to the property search request received in the step S10 (S12). That is, the search unit 523 transmits at least a part of the search condition included in the property search request to the property information DB 60 through the network N and receives a plurality of property candidates as a search result from the property information DB 60.

Figure 5:
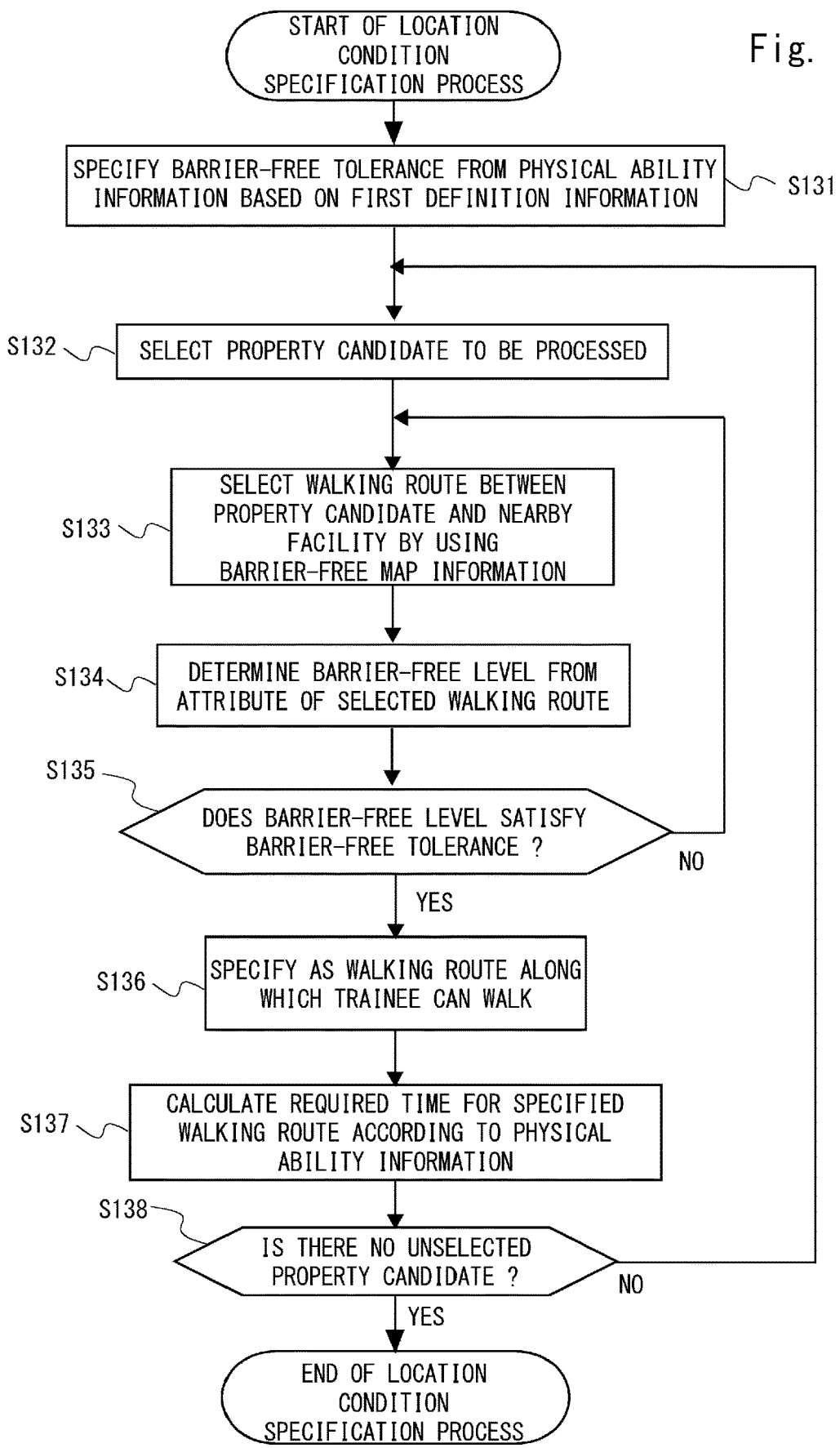
FIG. 5 is a flowchart showing a flow of a location condition specification process according to the first embodiment.

The specification unit 524 of the property searching apparatus 50 performs a location condition specification process (S13). FIG. 5 is a flowchart showing a flow of a location condition specification process according to the first embodiment. Firstly, the specification unit 524 specifies a barrier-free tolerance 5112 from the physical ability information acquired in the step S11 based on the first definition information 511 (S131).

Then, the specification unit 524 selects a property candidate to be processed from among the plurality of property candidates (S132). For example, the specification unit 524 selects an unselected property candidate from among the plurality of property candidates retrieved in the step S12 and performs below-described processes for the selected property candidate.

The specification unit 524 selects, by using the barrier-free map information 70, a walking route between the property candidate to be processed and the nearby facility (S133). For example, the specification unit 524, by using a node 71 and a route 73 in the barrier-free map information 70, specifies a walking route by using the nearby facility designated by the search condition as a start-point node and using the location at the address or the like of the property candidate to be processed as an end-point node. Note that there may be a plurality of walking routes linking between the start-point node and the end-point node, and in this example, it is assumed that an arbitrary (underived (i.e., unused)) walking route is selected.

Then, the specification unit 524 determines a barrier-free level from a sidewalk attribute of the selected walking route (S134). Specifically, the specification unit 524 acquires an attribute 74 associated with the selected walking route (the route 73) from the barrier-free map information 70 and determines a barrier-free level from the attribute 74. For example, a table in which attributes of routes are associated with barrier-free levels is stored in advance in the storage unit 51, and the specification unit 524 may specify a barrier-free level from the attribute 74 by referring to this table.

After that, the specification unit 524 determines whether or not the determined barrier-free level satisfies the barrier-free tolerance 5112 specified in the step S131 (S135). For example, when the barrier-free level is equal to or higher than a threshold indicated by the barrier-free tolerance, the specification unit 524 determines that the barrier-free level satisfies the barrier-free tolerance. When it is determined that the barrier-free level does not satisfy the barrier-free tolerance in the step S135, the process returns to the step S133. Then, the specification unit 524 selects a walking route between the property candidate to be processed and the nearby facility by using the barrier-free map information 70 again. In this case, a walking route that has not been selected so far is selected. Similarly, the specification unit 524 determines a barrier-free level in the step S134 and determines whether or not the determined barrier-free level satisfies the barrier-free tolerance 5112 in the step S135.

When it is determined that the barrier-free level satisfies the barrier-free tolerance in the step S135, the specification unit 524 specifies the selected walking route as a walking route along which the trainee 10 can walk (S136). Then, the specification unit 524 calculates a time required to travel along the specified walking route (hereinafter also referred to as the required time or the required travel time) according to the physical ability information (S137) and specifies the calculated required time as a location condition. For example, it is assumed that a table defining required times corresponding to combinations of physical ability information, barrier-free levels, and lengths of walking routes is stored in advance in the storage unit 51. In this case, firstly, the specification unit 524 specifies a length of the walking route specified in the step S136 from the route 73 and the attribute 74 in the barrier-free map information 70. Then, the specification unit 524 may obtain a required time corresponding to a combination of the physical ability information acquired in the step S11, the barrier-free level determined in the step S134, and the length of the specified walking route by referring to the table. Alternatively, the specification unit 524 may be equipped with calculation logic for calculating a required travel time based on the physical ability information, the barrier-free level, and the length of the walking route, and may calculate the required time by using the calculation logic. Note that in the step S138, instead of using the required time, a distance (a length of the specified walking route) between the property candidate and the nearby facility may be used as the location condition. Further, the specification unit 524 associates the walking route specified in the step S136 with the location condition (the required time or the distance calculated in the step S137) and stores them in the storage unit 51 or the memory 53.

After that, the specification unit 524 determines whether or not there is no unselected property candidate among the plurality of property candidates (S138). When it is determined that there is an unselected property candidate (No at S138), the process returns to the step S132 and the process therein and those in the subsequent steps are performed. On the other hand, when it is determined that there is no unselected property candidate in the step S138 (Yes at S138), the location condition specification process is finished and the process proceeds to a step S14. Note that in the following description, it is assumed that two or more property candidates have been retrieved (i.e., found) in the step S12. That is, at this stage, it is assumed that two or more combinations of property candidates and location conditions are held in the storage unit 51 or the memory 53.

The description is continued by referring to FIG. 4 again. The output unit 525 sorts (i.e., rearrange) a plurality of property candidates according to the location condition (S14). In this case, the output unit 525 sorts the plurality of property candidates so that the better the location condition is, the higher the corresponding property candidate is ranked in the sorted list of property candidates. The fact that the location condition is better means, for example, the required travel time or the distance between the property candidate and the nearby facility is shorter.

Then, the output unit 525 outputs the sorted list of property candidates (S15). For example, the output unit 525 transmits the sorted list of property candidates to the trainee terminal 40 that has issued the property search request through the network N. In this way, a user on the trainee side can recognize property candidates to which the trainee 10 may move in a priority-based order that is determined according to the location condition corresponding to his/her after-training physical ability.

Figure 6:
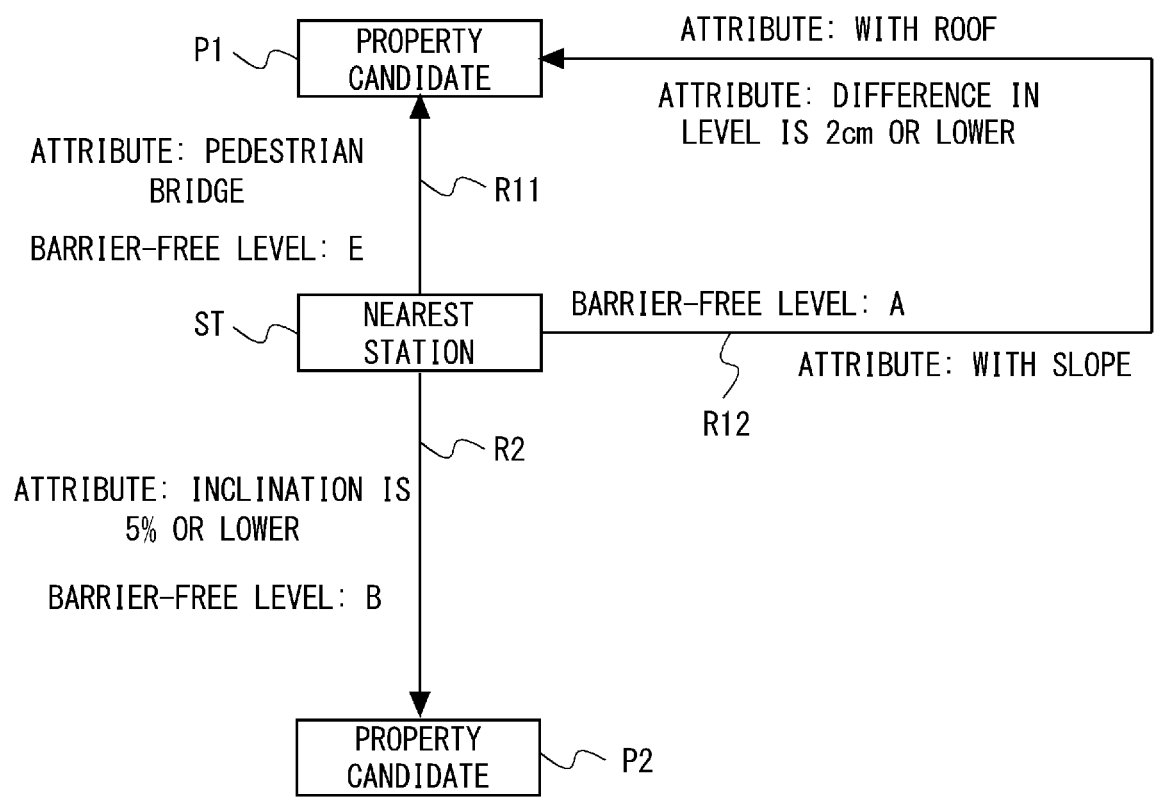
FIG. 6 shows an example of different walking routes according to the physical ability in accordance with the first embodiment.

Here, FIG. 6 shows an example of different walking routes according to the physical ability in accordance with the first embodiment. A nearest station ST is an example of a nearby facility included in the search condition of the property search request received in the step S10. In the case of an ordinary property search site, the location conditions of property candidates P1 and P2 are the distances of the shortest routes between the nearest station ST and the property candidates P1 and P2 or the times required to travel along the shortest routes at a normal walking speed of an ordinary person. In the example shown in FIG. 6, the shortest route between the nearest station ST and the property candidate P1 is a walking route R11, and the shortest route between the nearest station ST and the property candidate P2 is a walking route R2. Further, the distance of the walking route R11 is shorter than that of the walking route R2 and its required time is also shorter than that of the walking route R2. Therefore, in the ordinary property search site, regarding the location condition based on the nearest station ST, the property candidate P1 is better than the candidate P2. Therefore, in the search result, the property candidate P1 is displayed at a position higher than that of the candidate P2.

In contrast to this, in this embodiment, for example, the barrier-free tolerance is specified as a tolerance B based on the physical ability information of the trainee 10 (S131). Further, when the attribute of the walking route R11 is a pedestrian bridge, its barrier-free level is determined to be a level E (S134). Further, in this case, the barrier-free level E of the walking route R11 does not satisfy the barrier-free tolerance B of the trainee 10 (No at S135). That is, it is determined that, for the trainee 10, the walking route R11 is not suitable for the walking route between the nearest station ST and the property candidate P1. Therefore, the specification unit 524 selects a walking route R12 as another walking route between the nearest station ST and the property candidate P1 (S133). Further, when the attributes of the walking route R12 are that it is equipped with a slope, that a difference in level is 2 cm or lower, and that it is roofed, the specification unit 524 determines that its barrier-free level is a level A (S134). In this case, the barrier-free level A of the walking route R12 satisfies the barrier-free tolerance B of the trainee 10 (Yes at S135). Therefore, the walking route R12 is specified as a walking route along which the trainee 10 can walk (S136) and its required time is calculated according to the physical ability information (S127).

Meanwhile, it is assumed that the attribute of the walking route R2 is an inclination of 5% or lower and its barrier-free level is a level B. Further, the distance or the required time of the walking route R12 is longer than the distance or the required time of the walking route R2. Therefore, in this embodiment, regarding the location condition based on the nearest station ST, the property candidate P2 is better than the candidate P1. Therefore, in the search result, the property candidate P2 is displayed at a position higher than that of the candidate P1. That is, it is possible to change the location condition of the property candidate according to the physical ability information of the trainee 10. Therefore, it is possible to display the search result in a priority-based order according to the physical ability based on the sorting result according to the location condition.

Therefore, according to this embodiment, it is possible to easily retrieve (i.e., find) an appropriate property according to the physical ability of a trainee who has performed rehabilitation in order to restore or maintain his/her physical ability.

Second Embodiment

Figure 7:
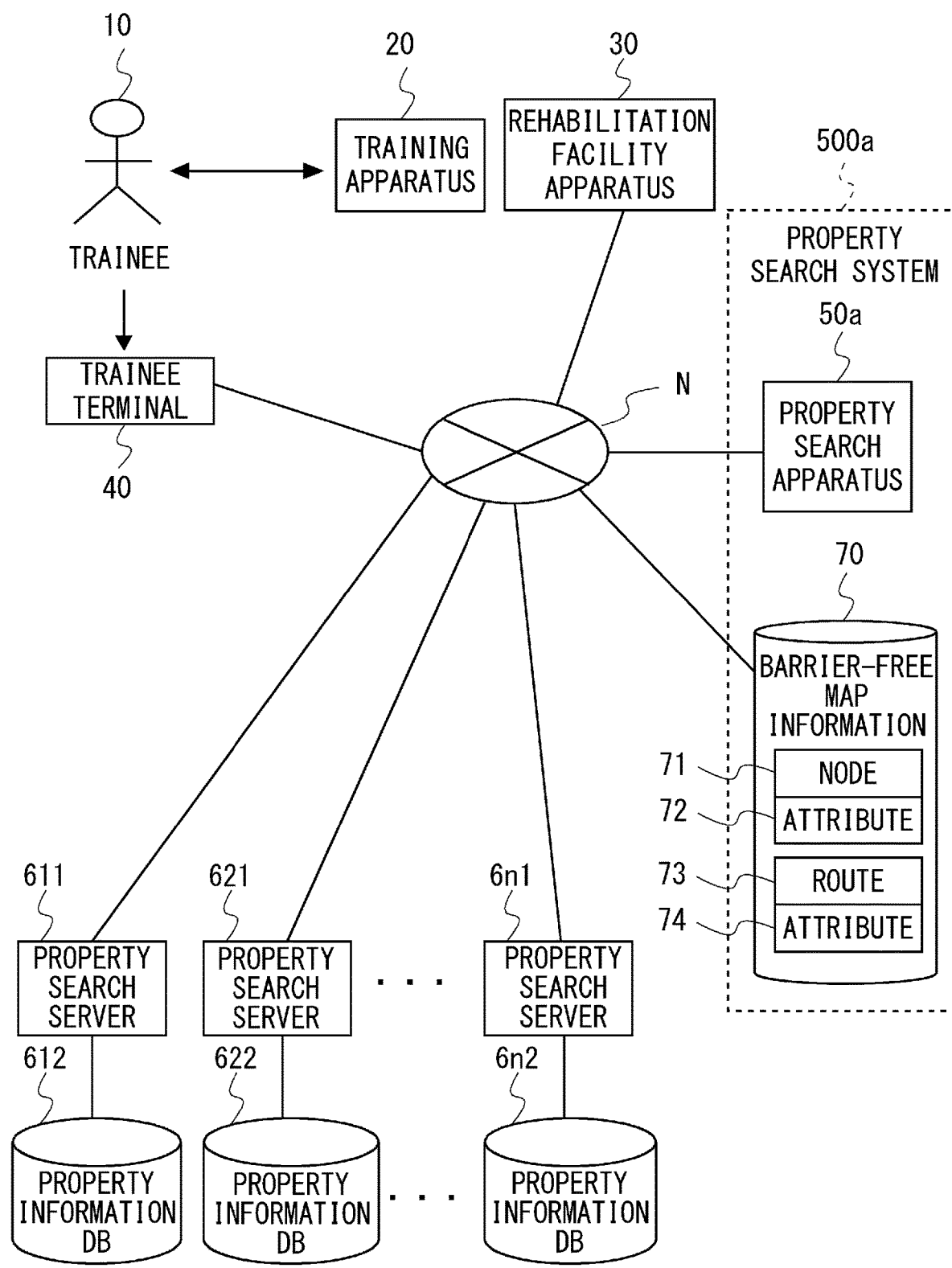
FIG. 7 is a block diagram showing an overall configuration of a property search system according to a second embodiment.

A second embodiment is a modified example of the above-described first embodiment. FIG. 7 is a block diagram showing an overall configuration including a property search system 500a according to the second embodiment. In FIG. 7, the property search apparatus 50 and the property information DB 60 shown in FIG. 1 are replaced by a property search apparatus 50a and property information DBs 612, 622, . . . , and 6n2 (n is an integer no smaller than two). Further, property search servers 611, 621, . . . , and 6n1 are installed for the respective property information DBs. Note that the rest of the configuration is substantially identical to that of the first embodiment, and therefore descriptions of the common components/structures are omitted.

Each of the property search servers 611 to 6n1 is connected to the property search system 500a and the like through the network N. Further, each of the property search servers 611 to 6n1 is connected to a corresponding one of the property information DBs 612 to 6n2. The property search servers 611 to 6n1 are ordinary property search sites managed by different real estate agents. Therefore, the property search servers 611 to 6n1 may have formats different from each other for individual property search requests. Further, it is also assumed that at least parts of the contents of the property information DBs 612 to 6n2 are different from each other. That is, they have different property information pieces for the same property candidate, or their search results may be different from each other even when the same search condition is used.

For example, when the property search server 611 receives an individual property search request in conformity with the format of its own site from the property search apparatus 50a through the network N, it searches the property information DB 612 according to the received individual property search request. Then, the property search server 611 acquires a plurality of property candidates as a search result from the property information DB 612 and sends back the search result to the property search apparatus 50a through the network N. The same applies to each of the property search servers 621 to 6n1.

Figure 8:
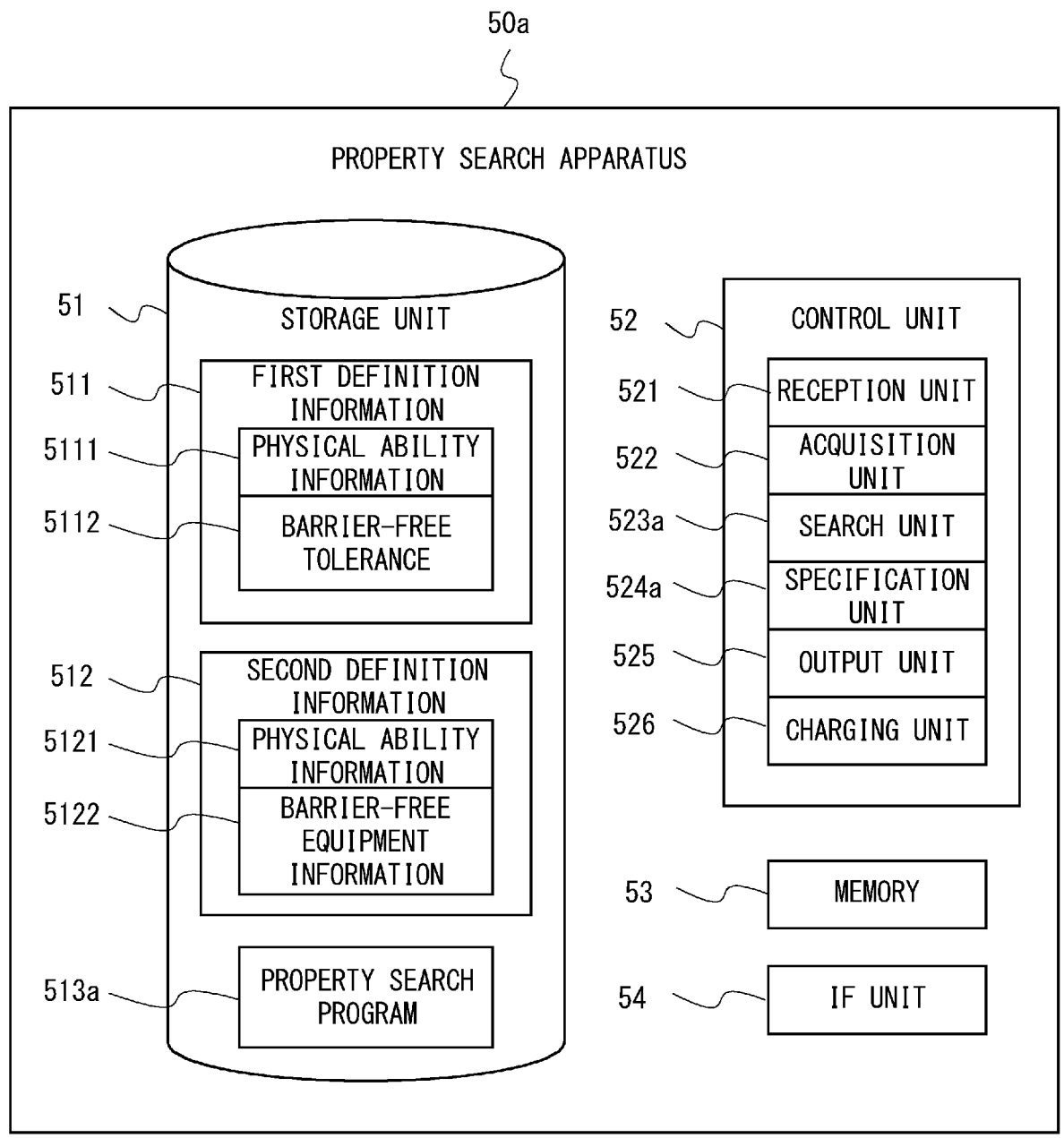
FIG. 8 is a block diagram showing a configuration of a property search apparatus according to the second embodiment.

FIG. 8 is a block diagram showing a configuration of the property search apparatus 50a according to the second embodiment. In FIG. 8, the property search program 513, the search unit 523, and the specification unit 524 shown in FIG. 2 are replaced with a property search program 513a, a search unit 523a, and a specification unit 524a. Further, a charging unit 526 is added in FIG. 8. Note that the rest of the configuration is substantially identical to that of the first embodiment, and therefore descriptions of the common components/structures are omitted.

The property search program 513a is a computer program in which processes that are performed in a method for searching for a property according to the second embodiment are implemented.

The search unit 523a transmits at least a part of the property search request to a predetermined property search server(s) and receives a plurality of property candidates as a search result from the property search server(s). In particular, the search unit 523a generates a plurality of individual property search requests each of which corresponds to a respective one of at least two property search servers 611 to 6n1 from the at least the part of the property search request, and transmits the generated individual property search requests to the respective property search servers.

The specification unit 524a specifies a location condition for each of the plurality of property candidates retrieved by at least the above-described predetermined property search server(s). In this way, there is no need to manage any property information DB in the property search system 500a. That is, it is possible to search the latest property information by using an external property information DB(s). In particular, the specification unit 524a makes a plurality of property candidates by combining search results received from respective property search servers. In this way, it is possible to provide an aggregation service by using a plurality of external property search servers.

When a contract is made with a user on the trainee side including the trainee 10 for a property candidate included in the search result output by the output part 525, the charging unit 526 charges the property search server that has retrieved the property candidate for which the contract has been made. In this way, it is possible to effectively obtain a monetary value for an added value that the search result is provided based on the location condition in which the physical ability is also taken into consideration as compared to search results of ordinary property search sites.

Figure 9:
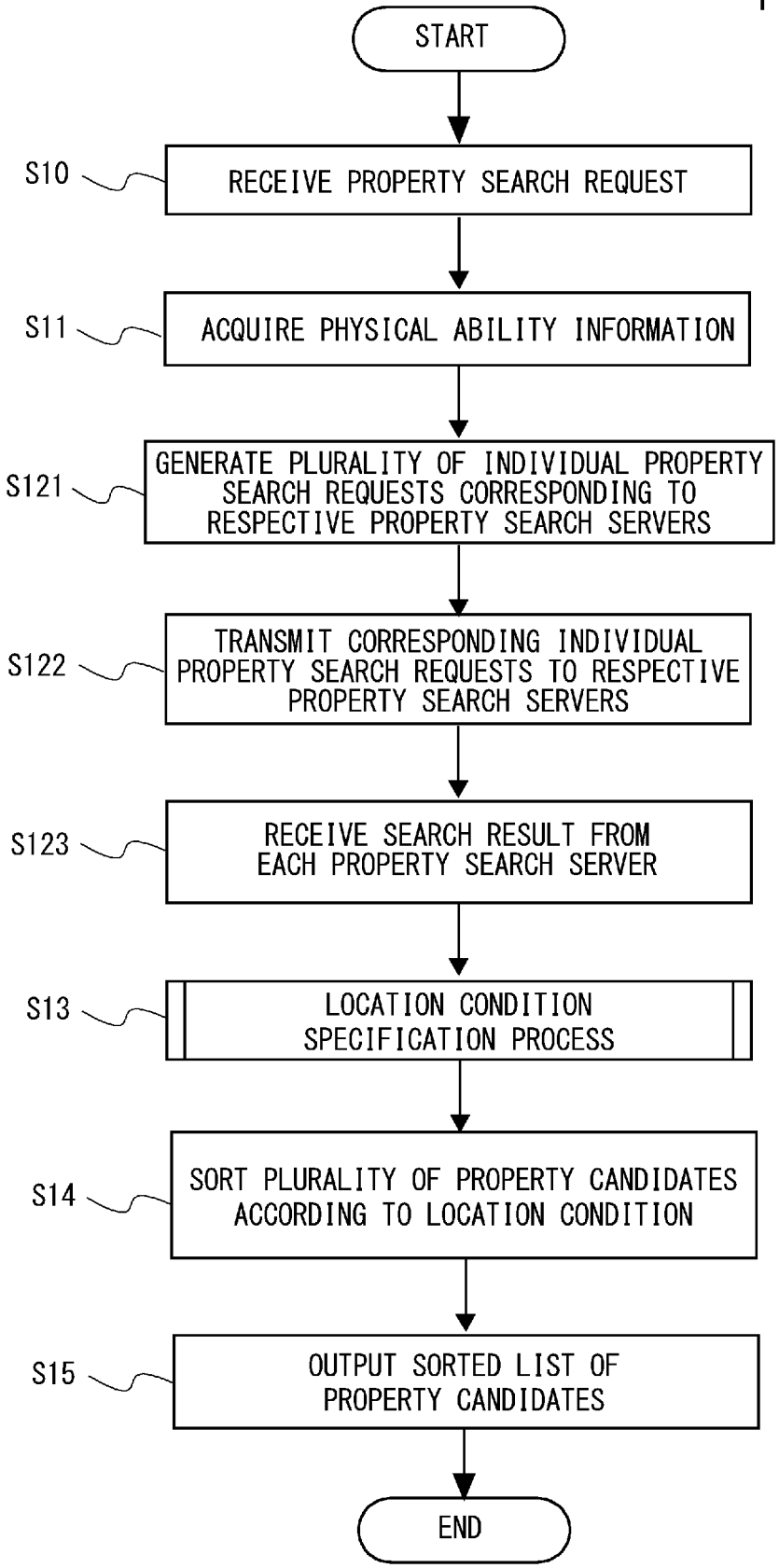
FIG. 9 is a flowchart showing a flow of a property search process according to the second embodiment.

FIG. 9 is a flowchart showing a flow of a property search process according to the second embodiment. In FIG. 9, the step S12 shown in FIG. 4 is replaced by steps S121 to S123. Note that the other steps are similar to those shown in FIG. 4 and therefore their descriptions are omitted.

After the step S11, the search unit 523a generates a plurality of individual property search requests corresponding to the respective property search servers 611 to 6n1 (S121). Note that it is assumed that the search unit 523a holds beforehand formats (such as forms, parameters, and protocols) of property search requests for the respective property search servers 611 to 6n1. Therefore, the search unit 523a generates a plurality of individual property search requests by using at least a part of the search condition of the property search request received in the step S10 and converting it into formats each of which corresponds to a respective one of the property search servers.

Then, the search unit 523a transmits a corresponding one of the generated individual property search requests to a respective one of the property search servers 611 to 6n1 (S122). Then, the search unit 523a receives a search result from each of the property search servers 611 to 6n1 (S123). After that, the specification unit 524a makes the plurality of property candidates as described in the step S13 by combining the search results received from the respective property search servers. Note that the specification unit 524a may combine property information pieces while handling property candidates that are same as each other but included in different search results as the same property candidate.

Figure 10:
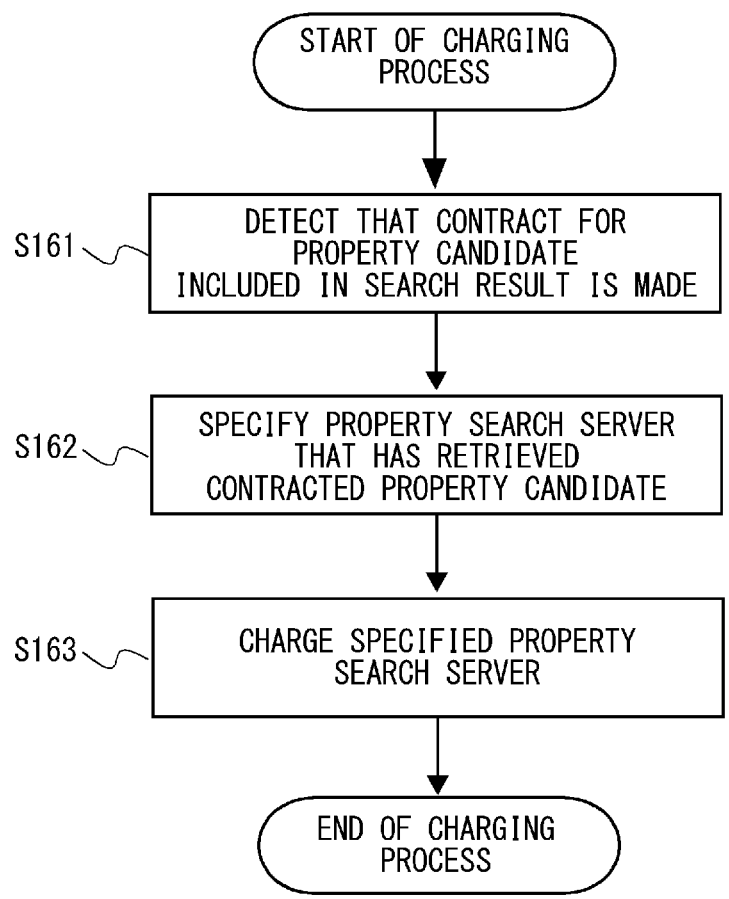
FIG. 10 is a flowchart showing a flow of a charging process according to the second embodiment.

FIG. 10 is a flowchart showing a flow of a charging process according to the second embodiment. In this example, for example, it is assumed that a user on the trainee side has made a lease contract for one property included in the property candidate list obtained in the step S15. In this case, the trainee terminal 40 sends, according to an operation performed by the user on the trainee side, a notification indicating identification information of the contracted property, a date and time at which the search result is output, an amount of money for the contract, and the like to the property search apparatus 50a through the network N. Alternatively, the notification may be sent from an agent terminal (not shown) operated by a real estate agent that has mediated (i.e., helped) the lease contract. Note that it is assumed that the property search apparatus 50a stores a history of search results in the storage unit 51 or the like.

Note that upon receiving the notification, the charging unit 526 detects (i.e., recognizes) that a contract for the property candidate included in the search result obtained in the step S15 has been made (S161). Then, the charging unit 526 specifies a property search server that has retrieved the property candidate for which the contract has been made (S162). For example, the charging unit 526 refers to the above-described history of search results and thereby specifies the property search server, which has retrieved the property candidate for which the contract has been made, based on the identification information of the property, the date and time at which the search result is output, and the like included in the notification. After that, the charging unit 526 charges the specified property search server (S163). For example, the charging unit 526 calculates an amount of money that a person (or a company) who manages the property search server is charged from the amount of money or the like for the contract included in the notification by using an arbitrary calculation formula or the like. Then, the charging unit 526 stores the identification information of the property search server and charging management information including the charged amount of money in the storage unit 51. In this way, a charging system or the like (not shown) of the property search system 500a can separately (e.g., later) charge the person (or the company) who manages the property search server the amount of money based on the charging management information. Note that the charging unit 526 may transmit information for charging the amount of money or the like to the specified property search server through the network N.

As described above, according to the second embodiment, it is possible to search the latest property information by using an external property information DB(s). In particular, by summarizing search results of a plurality of external property search servers as described above, it is possible to obtain more complete property candidates and thereby provide a search result based on the location condition in which the physical ability is taken into consideration. Further, it is possible to make a profit from such an aggregation service.

Third Embodiment

A third embodiment is an improved example of the above-described first or second embodiment and provides a mechanism for updating the barrier-free map information 70. An improved example of the first embodiment will be described hereinafter. However, it is also applicable to the second embodiment.

Figure 11:
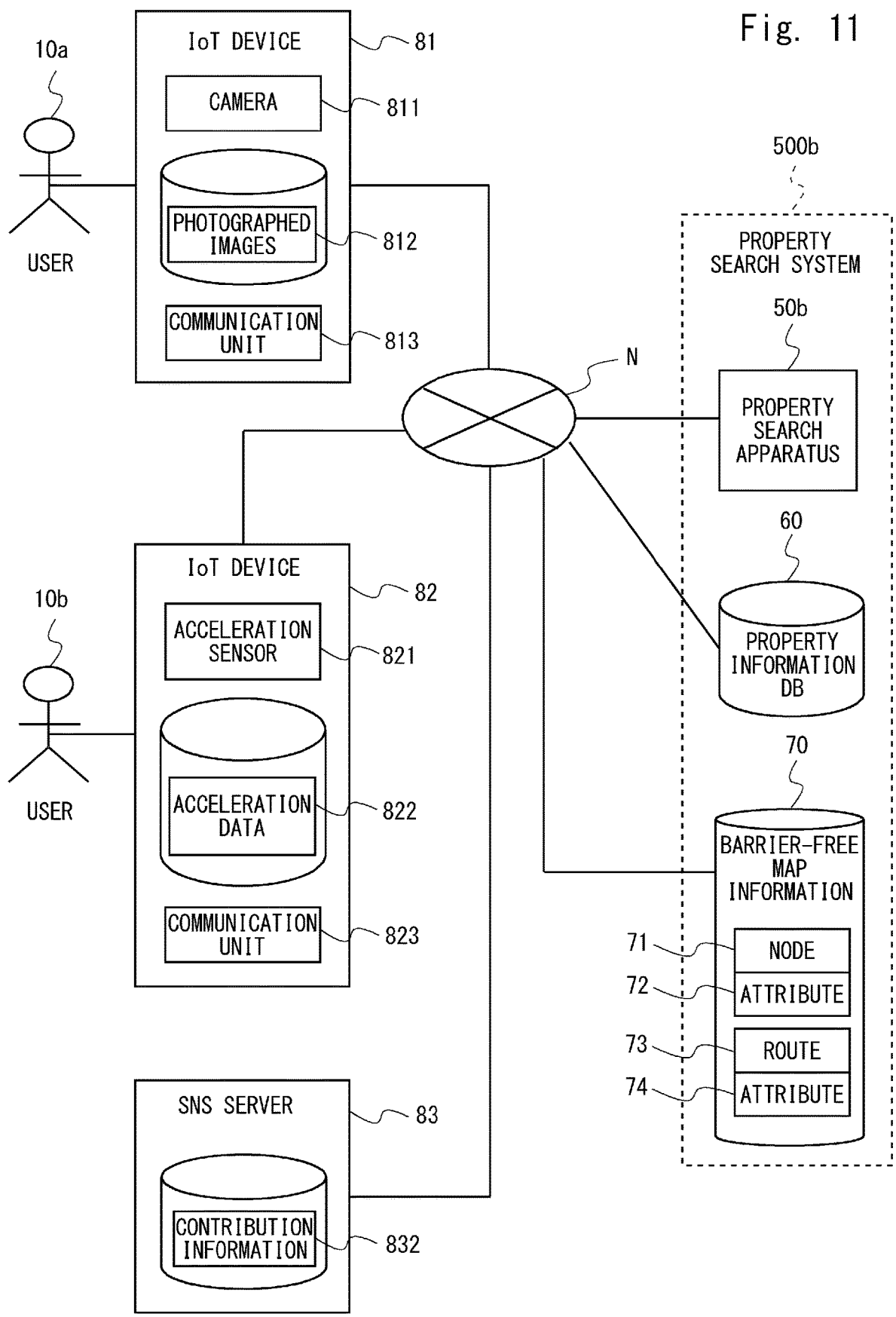
FIG. 11 is a block diagram showing an overall configuration of a property search system according to a third embodiment.

FIG. 11 is a block diagram showing an overall configuration including a property search system 500b according to the third embodiment. In FIG. 11, the property search apparatus 50 shown in FIG. 1 is replaced by a property search apparatus 50b. Further, IoT (Internet of Things) devices 81 and 82 and an SNS (Social Networking Service) server 83 are added in FIG. 11. Note that the rest of the configuration is substantially identical to that of the first embodiment, and therefore the drawing and the description thereof are omitted. Note that users 10a and 10b may be ordinary people or persons who are somewhat disabled in regard to the physical ability compared to ordinary people.

The IoT device 81 is a device that moves together with the user 10a and can communicate with the property search apparatus 50b or the like through the network N. The IoT device 81 includes a camera 811, photographed images 812, and a communication unit 813. The camera 811 photographs surroundings of the IoT device 81 and stores photographed images 812 in a storage device disposed inside the IoT device 81. Note that it is assumed that the photographed image 812 includes at least a part of a sidewalk. The communication unit 813 has a function of communicating through the network N and transmits photographed images 812 to the property search apparatus 50b through the network N at predetermined intervals or in response to a request from the property search apparatus 50b.

The IoT device 81 may be, but is not limited to, a drive recorder, a smartphone, personal mobility, or a camera device attached to a wheelchair. When the IoT device 81 is a drive recorder, the IoT device 81 is disposed in an automobile on which the user 10a rides. In this case, the photographed images 812 may be images that are taken by the camera 811 and include a sidewalk near a road on which the automobile is traveling. When the IoT device 81 is a smartphone, the photographed images 812 are images that are taken when the user 10a is walking. When the IoT device 81 is personal mobility, the photographed images 812 are images that are taken by the camera 811 when the user 10a is on the personal mobility and traveling thereby. When the IoT device 81 is a camera device attached to a wheelchair, the photographed images 812 are images including a sidewalk that the user 10a actually passed when he/she travels by using the wheelchair.

The IoT device 82 is a device that moves together with the user 10b and can communicate with the property search apparatus 50b or the like through the network N. The IoT device 82 includes an acceleration sensor 821, acceleration data 822, and a communication unit 823. The acceleration sensor 821 measures an acceleration when the IoT device 82 moves, and stores acceleration data 822 in a storage device disposed inside the IoT device 82. The communication unit 823 has a function of communicating through the network N and transmits acceleration data 822 to the property search apparatus 50b through the network N at predetermined intervals or in response to a request from the property search apparatus 50b.

The IoT device 82 may be, but is not limited to, a wearable apparatus, a smartphone, personal mobility, or an acceleration sensor device attached to a wheelchair. When the IoT device 82 is a wearable apparatus, the IoT device 81 is attached to the user 10b and the acceleration sensor 821 measures (i.e., obtains) acceleration data 822 when the user 10b is walking. The same applies to the other examples. Note that the photographed images 812 and the acceleration data 822 are examples of data that are acquired when the IoT device is being moved.

The SNS server 83 is an ordinary web system that provides an SNS on the Internet. In particular, the SNS server 83 is a server apparatus and stores contribution information 832 in its internal storage device. The contribution information 832 is text information, imaged, or the like written or drawn by users, related to information about sidewalks in various places. The SNS server 83 transmits the contribution information 832 to the property search apparatus 50b through the network N in response to a request from the property search apparatus 50b.

Figure 12:
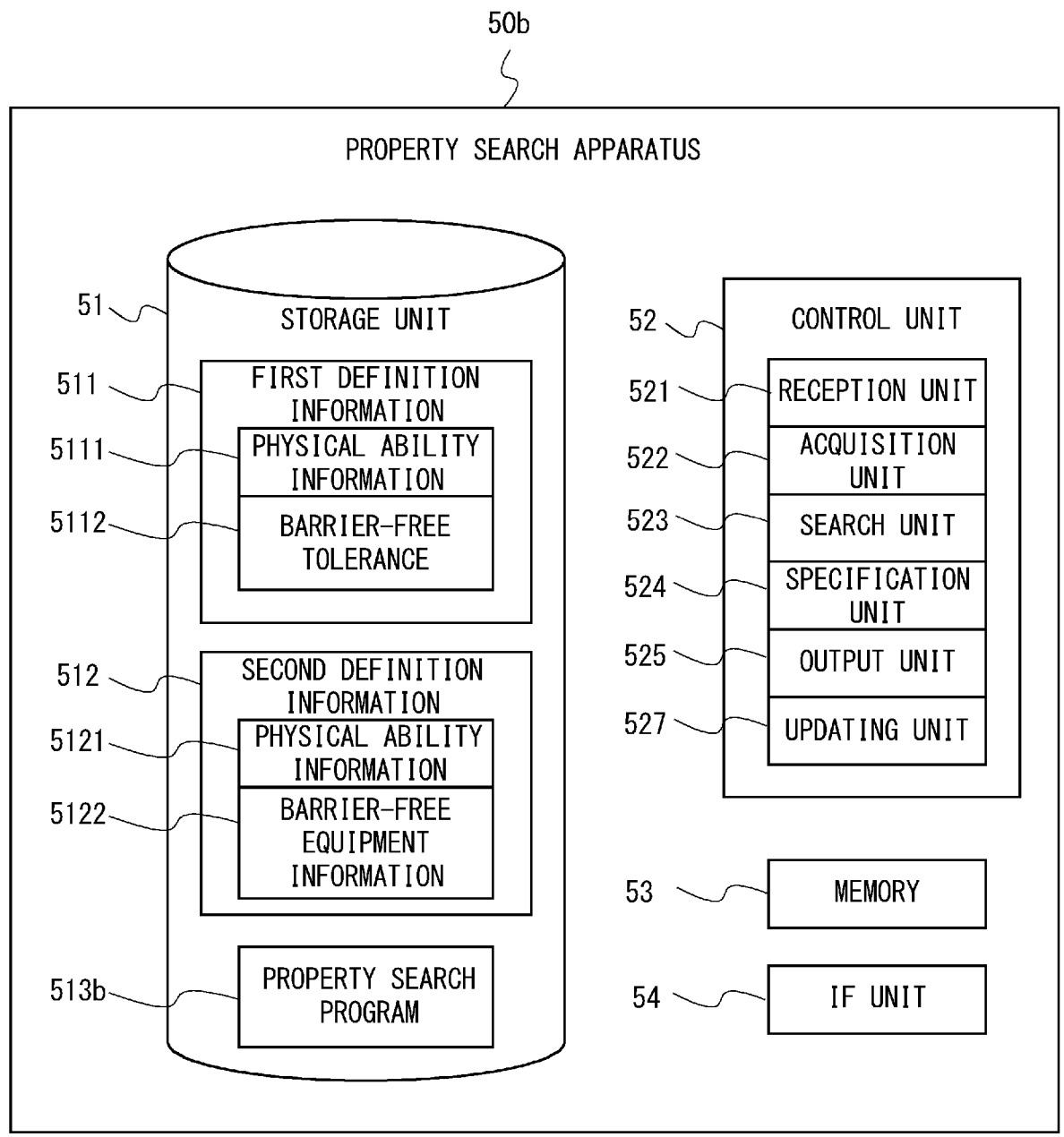
FIG. 12 is a block diagram showing a configuration of a property search apparatus according to the third embodiment.

FIG. 12 is a block diagram showing a configuration of a property search apparatus 50b according to the third embodiment. In FIG. 12, the property search program 513 shown in FIG. 2 is replaced by a property search program 513b. Further, an updating unit 527 is added in FIG. 12. Note that the rest of the configuration is substantially identical to that of the first embodiment, and therefore descriptions of the common components/structures are omitted.

The property search program 513b is a computer program in which processes that are performed in a method for searching for a property according to the third embodiment are implemented.

The updating unit 527 is an example of the first and second updating units. For example, the updating unit 527 collects photographed images 812 from the IoT device 81 through the network N, extracts an attribute(s) of a sidewalk (s) from the photographed images 812, and updates the attribute 74 of the barrier-free map information 70. In this case, the updating unit 527 extracts an area of a sidewalk by analyzing the photographed images 812, and extracts it as an attribute of the sidewalk based on the shape and the like in the extracted area of the sidewalk. For example, the updating unit 527 can extract attributes such as a slope, a roof, a pedestrian bridge, and a pedestrian crossing from the area of the sidewalk.

Further, the updating unit 527 collects acceleration data 822 from the IoT device 82 through the network N, extracts an attribute(s) of a sidewalk(s) from the acceleration data 822, and updates the attribute 74 of the barrier-free map information 70. In this case, the updating unit 527 can extract an inclination or the like of the sidewalk as an attribute from the acceleration data 822.

Further, the updating unit 527 transmits a request to acquire contribution information 832 (hereinafter also referred to as the acquisition request) to at least one SNS server 83 through the network N, and collects contribution information 832 from the SNS server(s) 83. Then, the updating unit 527 analyzes, for example, text information of the contribution information 832 and thereby extracts a condition(s) of the sidewalk such as an address of the sidewalk, information as to how easily a wheelchair can pass the sidewalk, and a congestion state of the sidewalk. Alternatively, the updating unit 527 analyzes, for example, image information of the contribution information 832 in a manner similar to that for the photographed image 812, and thereby extracts an attribute(s) or a condition(s) of the sidewalk. Further, the updating unit 527 updates the attribute 74 of the barrier-free map information 70 by using the extracted attribute or the condition of the sidewalk.

Figure 13:
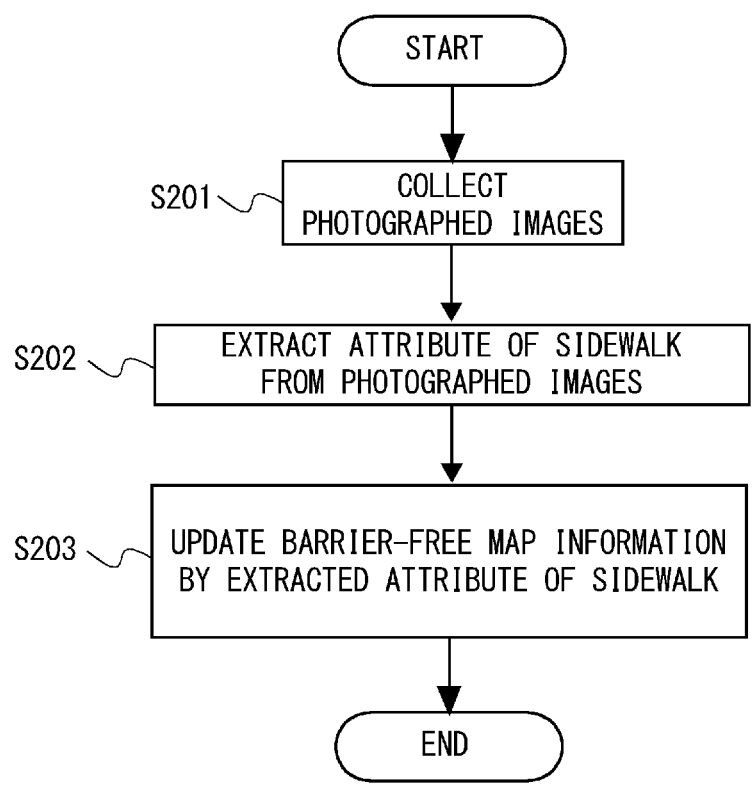
FIG. 13 is a flowchart showing a flow of a barrier-free map information updating process according to the third embodiment.

FIG. 13 is a flowchart showing a flow of a barrier-free map information updating process according to the third embodiment. An example in which photographed images 812 are collected from the IoT device 81 will be described hereinafter. However, the same applies to cases where data is collected from the IoT device 82 or the SNS server 83.

Firstly, the updating unit 527 transmits an acquisition request for photographed images 812 to at least one IoT device 81 through the network N in response to a predetermined trigger. Then, the updating unit 527 receives and collects the photographed images 812 from the IoT device 81 through the network N (S201). Note that the updating unit 527 may collect photographed images 812 by receiving those that are transmitted from at least one IoT device 81 at regular intervals. Further, the updating unit 527 may accumulate collected photographed images 812 in the storage unit 51.

Next, the updating unit 527 extracts an attribute(s) of a sidewalk(s) from the photographed images 812 (S202). Then, the updating unit 527 updates the attribute 74 of the barrier-free map information 70 by using the extracted attribute(s) of the sidewalk(s) (S203).

As described above, according to the third embodiment, it is possible to automatically update the barrier-free map information 70. Therefore, it is possible to efficiently extend the range of the barrier-free map information 70 and efficiently improve the accuracy thereof. In particular, in the case where the user 10a or 10b is somewhat disabled in regard to the physical ability as compared to ordinary people, since the attributes become those related to routes along which the user having his/her physical ability has actually walked by using the harness, they can be considered to be information having very good quality as the barrier-free map information 70.

Fourth Embodiment

A fourth embodiment is an improved example of the above-described first to third embodiments. Note that a configuration of a property search system according to the fourth embodiment is substantially identical to that shown in FIG. 1 or the like. Therefore, a drawing thereof is omitted and descriptions of the common components/structures are also omitted.

Figure 14:
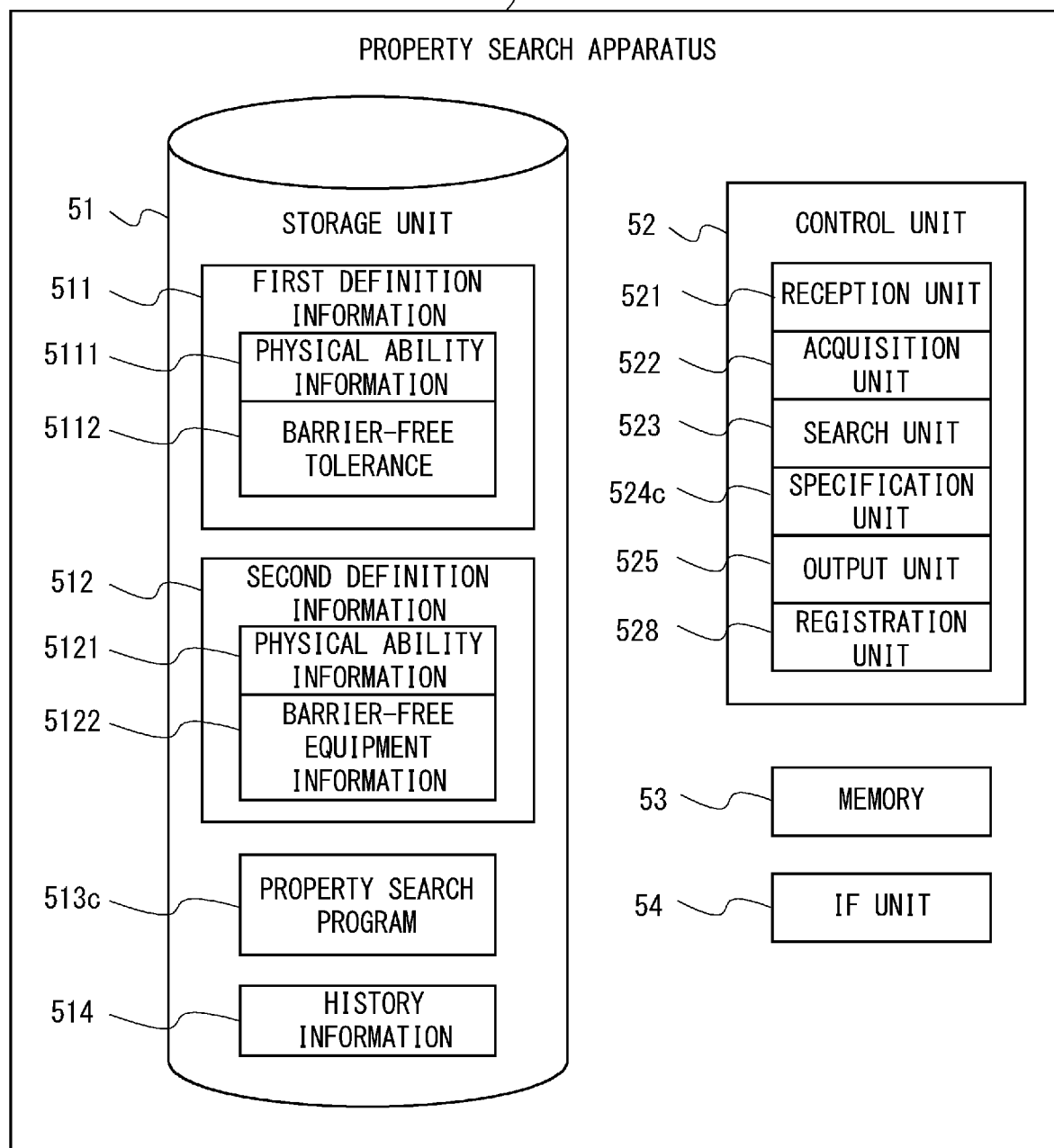
FIG. 14 is a block diagram showing a configuration of a property search apparatus according to a fourth embodiment.

FIG. 14 is a block diagram showing a configuration of a property search apparatus 50c according to the fourth embodiment. In FIG. 14, the property search program 513 and the specification unit 524 shown in FIG. 2 are replaced by a property search program 513c and a specification unit 524c. Further, history information 514 and a registration unit 528 are added in FIG. 14. Note that the rest of the configuration is substantially identical to that of the first embodiment or the like, and therefore descriptions of the common components/structures are omitted.

The property search program 513c is a computer program in which processes that are performed in a method for searching for a property according to the fourth embodiment are implemented.

The history information 514 is information in which a property candidate for which a contract with a user on the trainee side including the trainee 10 has been made is associated with the physical ability information acquired by the acquisition unit 522. Note that the storage unit 51 is an example of the history storage device. Further, the history information 514 may be stored in a storage device other than the storage unit 51 disposed in the property search apparatus 50c, or in a history storage device such as an external storage device connected to the property search apparatus 50c through the network N.

When a contract with a user on the trainee side including the trainee 10 is made for a property candidate included in the search result output by the output unit 525, the registration unit 528 associates the property candidate for which the contract has been made with the physical ability information acquired by the acquisition unit 522 and registers them as history information 514 in the storage unit 51.

In addition to having the function of the specification unit 524, the specification unit 524c specifies a location condition(s) while taking the history information 514 into consideration.

Figure 15:
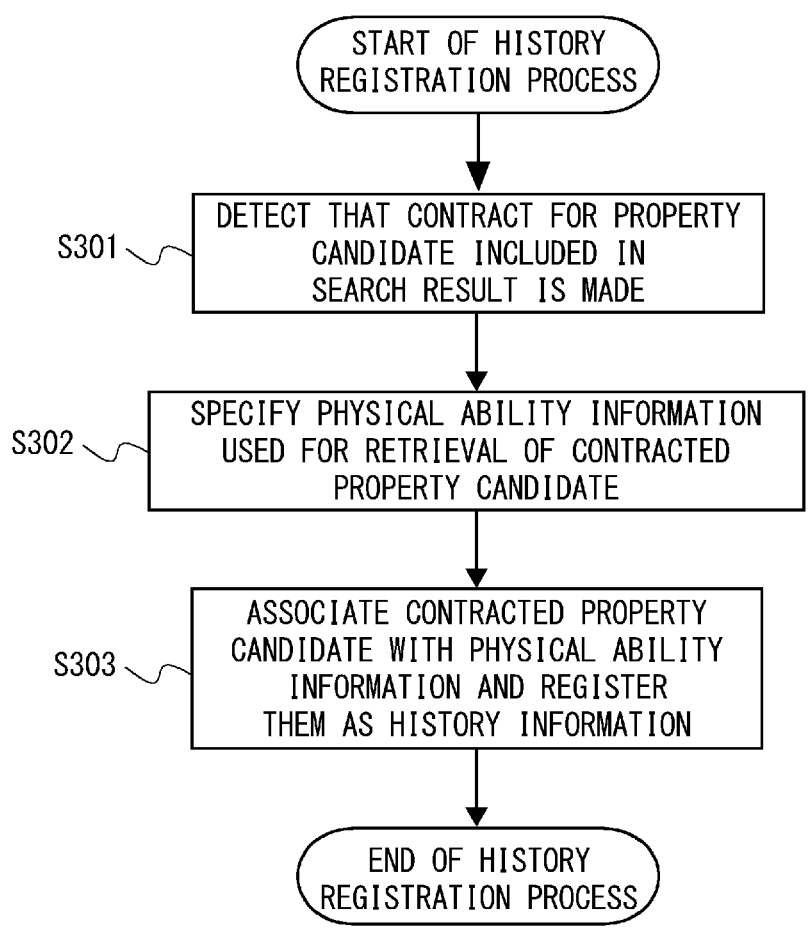
FIG. 15 is a flowchart showing a flow of a history registration process according to the fourth embodiment.

FIG. 15 is a flowchart showing a flow of a history registration process according to the fourth embodiment. In this example, for example, it is assumed that a user on the trainee side has made a lease contract for one property included in the property candidate list obtained in the step S15. In this case, the trainee terminal 40 sends, according to an operation performed by the user on the trainee side, a notification indicating identification information of the contracted property, a date and time at which the search result is output, an amount of money for the contract, and the like to the property search apparatus 50c through the network N. Alternatively, the notification may be sent from an agent terminal (not shown) operated by a real estate agent that has mediated (i.e., helped) the lease contract. Note that it is assumed that the property search apparatus 50c stores a history of combinations of search results and physical ability information in the storage unit 51 or the like.

Note that upon receiving the notification, the registration unit 528 detects (i.e., recognizes) that a contract for a property candidate included in the search result obtained in the step S15 has been made (S301). Then, the registration unit 528 specifies the physical ability information used for the property candidate for which the contract has been made (S302). For example, the registration unit 528 specifies the physical ability information by referring to the history of combinations of search results and physical ability information stored in the storage unit 51 or the like. Alternatively, when no physical ability information is stored in the storage unit 51 or the like and the identification information of the trainee 10 is included in the above-described notification, the acquisition unit 522 may acquire the physical ability information of the trainee 10 included in the above-described notification.

After that, the registration unit 528 associates the property candidate for which the contract has been made with the acquired physical ability information and registers them as history information 514 in the storage unit 51 (S303).

As described above, in the fourth embodiment, it is possible to, by taking the history information 514 into consideration, specify a better location condition for a property candidate for which a contract has been made based on past search results. Therefore, it is possible to retrieve an appropriate property according to the physical ability of a trainee more accurately.

OTHER EMBODIMENTS

Note that the present disclosure is not limited to the above-described embodiments and they can be modified as desired without departing from the spirit and scope of the present disclosure. Although the present disclosure is described as a hardware configuration in the above-described embodiments, the present disclosure is not limited to the hardware configurations. In the present disclosure, an arbitrary process can also be implemented by causing a CPU (Central Processing Unit) to execute a computer program.

In the above-described examples, the program can be stored and provided to a computer using any type of non-transitory computer readable media. Non-transitory computer readable media include any type of tangible storage media. Examples of non-transitory computer readable media include magnetic storage media (such as floppy disks, magnetic tapes, hard disk drives, etc.), optical magnetic storage media (e.g. magneto-optical disks), CD-ROM (compact disc read only memory), CD-R (compact disc recordable), CD-R/W (compact disc rewritable), DVD (Digital Versatile Disc), and semiconductor memories (such as mask ROM, PROM (programmable ROM), EPROM (erasable PROM), flash ROM, RAM (random access memory), etc.). The program may be provided to a computer using any type of transitory computer readable media. Examples of transitory computer readable media include electric signals, optical signals, and electromagnetic waves. Transitory computer readable media can provide the program to a computer through a wired communication line (e.g. electric wires, and optical fibers) or a wireless communication line.

From the disclosure thus described, it will be obvious that the embodiments of the disclosure may be varied in many ways. Such variations are not to be regarded as a departure from the spirit and scope of the disclosure, and all such modified examples as would be obvious to one skilled in the art are intended for inclusion within the scope of the following claims.

What is claimed is:

1. A property search system comprising:
a processor programmed to:
receive a property search request for a trainee who has performed training to restore or maintain his/her physical ability;
acquire physical ability information of the trainee;
specify, for each of a plurality of property candidates corresponding to the property search request, a location condition corresponding to the physical ability information by using a barrier-free map information; and output a search result of the property candidates according to the specified location condition by controlling a display to display the search result.

2. The property search system according to claim 1, further comprising a first storage that stores first definition information defining a barrier-free tolerance according to the physical ability, wherein
the processor specifies the barrier-free tolerance of the trainee from the acquired physical ability information based on the first definition information, and
the processor specifies, for each of the plurality of property candidates, the location condition by using the barrier-free map information so as to satisfy the specified barrier-free tolerance.

3. The property search system according to claim 2, wherein
the property search request includes a designation of a nearby facility in a vicinity of the property candidates,
the processor specifies, from among walking routes between each of the plurality of property candidates and the nearby facility in the barrier-free map information, a walking route that satisfies the specified barrier-free tolerance as a walking route along which the trainee can walk, and
the processor specifies the location condition based on the specified walking route.

4. The property search system according to claim 3, wherein
the barrier-free map information includes an attribute of the walking route, and
the processor specifies, from among the walking routes between each of the plurality of property candidates and the nearby facility, a walking route whose attribute satisfies the specified barrier-free tolerance as the walking route along which the trainee can walk.

5. The property search system according to claim 1, wherein
the property search request includes a designation of a nearby facility in a vicinity of the property candidates,
the processor specifies a walking route between each of the plurality of property candidates and the nearby facility in the barrier-free map information based on the physical ability information, the walking route being a route along which the trainee can walk, and
the processor specifies the location condition based on the specified walking route.

6. The property search system according to claim 3, wherein the processor calculates, for the specified walking route, a time required for the trainee to move along the specified walking route according to the physical ability information, and specifies the calculated required time as the location condition.

7. The property search system according to claim 1, wherein the processor is further programmed to transmit at least a part of the property search request to a property search server and receive the plurality of property candidates from the property search server, and
the processor specifies the location condition for each of the plurality of retrieved property candidates.

8. The property search system according to claim 7, wherein
the processor generates, from the at least the part of the property search request, a plurality of individual property search requests each of which corresponds to a respective one of two or more property search servers, and transmits, to each of the property search servers, its corresponding individual property search request, and
the processor generates the plurality of property candidates by combining search results received from the property search servers.

9. The property search system according to claim 7, wherein the processor is programmed to, when a contract is made with a trainee side including the trainee for a property candidate included in the search result, charge the property search server that has retrieved the property candidate for which the contract has been made.

10. The property search system according to claim 1, wherein the processor is programmed to:
when a contract is made with a trainee side including the trainee for a property candidate included in the search result, associate the property candidate for which the contract has been made with the acquired physical ability information and store them in a history storage device, and
the processor specifies the location condition by further taking information stored in the history storage device into consideration.

11. The property search system according to claim 1, wherein the processor is further programmed to collect data through a network, extract an attribute of a sidewalk from the collected data, and update the barrier-free map information, the data being data that is acquired when an IoT (Internet of Things) device is being moved.

12. The property search system according to claim 1, wherein the processor is further programmed to collect contribute information about sidewalks through a network, extract a condition of the sidewalk from the collected contribution information, and update the barrier-free map information.

13. The property search system according to claim 1, wherein
the processor further receives a request for an action as the trainee moves from a target property to a predetermined point, and
the processor specifies the location condition so as to satisfy the request for the action.

14. The property search system according to claim 1, further comprising:
a second storage that stores second definition information defining barrier-free equipment information according to the physical ability, wherein
the processor specifies the barrier-free equipment information from the acquired physical ability information based on the second definition information, and specifies property candidates each of which includes the barrier-free equipment information from among the plurality of property candidates, and
the processor outputs a search result of the property candidate from among the specified property candidates according to the specified location condition.

15. The property search system according to claim 1, wherein the physical ability information includes information about a harness used by the trainee.

16. A property search apparatus comprising:
a processor programmed to:
receive a property search request for a trainee who has performed training to restore or maintain his/her physical ability;
acquire physical ability information of the trainee;
specify, for each of a plurality of property candidates corresponding to the property search request, a location condition corresponding to the physical ability information by using a barrier-free map information; and output a search result of the property candidates according to the specified location condition by controlling a display to display the search result.

17. A method for searching for a property, comprising:

receiving, by a computer, a property search request for a trainee who has performed training to restore or maintain his/her physical ability;

acquiring, by the computer, physical ability information of the trainee;

specifying, by the computer, for each of a plurality of property candidates corresponding to the property search request, a location condition corresponding to the physical ability information by using a barrier-free map information; and outputting, by the computer, a search result of the property candidates according to the specified location condition by controlling a display to display the search result.

18. A non-transitory computer readable medium storing a property search program for causing a computer to execute steps comprising:

a process of receiving a property search request for a trainee who has performed training to restore or maintain his/her physical ability;

a process of acquiring physical ability information of the trainee;

a process of specifying for each of a plurality of property candidates corresponding to the property search request, a location condition corresponding to the physical ability information by using a barrier-free map information; and a process of outputting a search result of the property candidates according to the specified location condition by controlling a display to display the search result.

19. The property search system according to claim 1, wherein the processor acquires the physical ability information of the trainee by acquiring a first index value associated with the trainee that correlates with physical ability, and acquiring a second index value associated with the trainee that correlates with physical ability, and the processor determines a barrier-free tolerance of the trainee based on the first index value and the second index value, and the processor specifies the location condition based on the determined barrier-free tolerance.

* * * * *